(12) United States Patent
Koh et al.

(10) Patent No.: US 8,951,511 B2
(45) Date of Patent: Feb. 10, 2015

(54) COMPOSITIONS FOR IMPROVING MIGRATION POTENTIAL OF STEM CELLS

(75) Inventors: Seong Ho Koh, Seongnam-Si (KR); Seung Hyun Kim, Seoul (KR); Goang Won Cho, Seoul (KR); Min Young Noh, Seoul (KR); Kyung Suk Kim, Seoul (KR)

(73) Assignee: Corestem Co., Ltd., Chungcheongbuk-do (KR)

( * ) Notice: Subject to any disclaimer, the term of this patent is extended or adjusted under 35 U.S.C. 154(b) by 105 days.

(21) Appl. No.: 13/502,806

(22) PCT Filed: Oct. 19, 2010

(86) PCT No.: PCT/KR2010/007152
§ 371 (c)(1),
(2), (4) Date: Apr. 19, 2012

(87) PCT Pub. No.: WO2011/049346
PCT Pub. Date: Apr. 28, 2011

(65) Prior Publication Data
US 2012/0207724 A1    Aug. 16, 2012

(30) Foreign Application Priority Data
Oct. 19, 2009    (KR) .................. 10-2009-0099146

(51) Int. Cl.
| | | |
|---|---|---|
| *A01N 63/00* | (2006.01) |
| *A61K 48/00* | (2006.01) |
| *C12N 15/00* | (2006.01) |
| *C12N 15/86* | (2006.01) |
| *C12N 5/00* | (2006.01) |
| *C12N 5/02* | (2006.01) |
| *C12N 15/88* | (2006.01) |
| *A61K 35/28* | (2006.01) |
| *C07K 14/47* | (2006.01) |
| *A61K 38/00* | (2006.01) |

(52) U.S. Cl.
CPC ............. *A61K 35/28* (2013.01); *C07K 14/47* (2013.01); *A61K 48/00* (2013.01); *C12N 2799/027* (2013.01); *A61K 38/00* (2013.01)
USPC ........ 424/93.21; 435/455; 435/456; 435/325; 435/320.1; 435/458

(58) Field of Classification Search
CPC ....... A61K 35/28; A61K 48/00; A61K 38/00; C07K 14/47
USPC ............ 424/93.21; 435/455, 456, 325, 320.1, 435/458
See application file for complete search history.

(56) References Cited

PUBLICATIONS

Za et al., J. of Cell Science, 119: 2654-2666, 2006.*
"Migration 101—An Introduction to Cell Migration," Accessed from https://www.cellmigration.org/science/ on Jun. 3, 2014.*
Smart et al., Circulation Res., 102: 1155-1168, 2008.*
Huh et al., "Upregulation of β-Pix Expression in Migrating Neural Stem Cells in the Rat Brain," Society for Neuroscience $33^{rd}$ Annual Meeting Abstracts. Presentation No. 885.9, Nov. 12, 2003.
Jones et al., "Role of Phospholipase Cγ1 in Cell Spreading Requires Association with β-Pix/GIT1-Containing Complex, Leading to Activation of Cdc42 and Rac1," Mol. Cell. Biol. 27:5790-5805, 2007.

* cited by examiner

*Primary Examiner* — Thaian N Ton
(74) *Attorney, Agent, or Firm* — Clark & Elbing LLP

(57) ABSTRACT

The present invention relates to a composition for improving the migration potential of a stem cell, a method for evaluating the migration potential of a stem cell and a method for screening an adjuvant of cell therapy improving the migration potential of a stem cell. The present invention may be effectively used for enhancing the efficacy of neurological disease-treatment by inducing therapeutic stem cells to migrate efficiently to the lesion site.

4 Claims, 19 Drawing Sheets

Fig. 2a

Gene expression relative to C-MSC

| | Gene Symbol | Other name | Gene function | Fold change |
|---|---|---|---|---|
| 1 | VEGFA | Vascular endothelial growth factor A | Angiogenesis, cell migration... | -23.05 |
| 2 | CTSK | Cathepsin K | Tumor metastasis | -8.94 |
| 3 | β-PIX | | Cancer cell migration | -7.582 |
| 4 | MTSS1 | Metastasis suppressor 1 | Lamellipodia assembly, metastasis | -6.03 |
| 5 | CXCL12 | Chemokine (C-X-C motif) ligand 12 | Chemokine | -5.76 |
| 6 | HPSE | Heparanase | Migration & invasion | -5.38 |
| 7 | SMAD2 | SMAD family member 2 | TGFb signaling | -5.38 |
| 8 | HGF | Hepatocyte growth factor | Migration | -3.89 |
| 9 | FLT4 | Fms-related tyrosine kinase 4 | Tyrosine kinase for VEGFc,d | -3.71 |
| 10 | ITGA7 | Integrin, alpha 7 | | -3.39 |
| 11 | MMP11 | Matrix metallopeptidase 11 | Tissue remodeling, metastasis | -3.47 |
| 12 | FN1 | Fibronectin 1 | Cell adhesion & migration | -2.51 |
| 13 | MTA1 | Metastasis associated 1 | expressed in metastatic cell | -2.45 |
| 14 | PTEN | Phosphatase and tensin homolog | Tumor suppressor by negatively regulating AKT/PKB | -2.45 |
| 15 | FXYD5 | FXYD domain containing ion transport regulator 5 | cancer prograssion, migration, invasion | -2.04 |

1) Western blot

2) Realtime-PCR

1) Western blot

β-PIX (5 min)

β-PIX (1 min)

β-actin

CON    GFP    hPIX

2) Realtime -PCR

ALS-MSC

ALS-MSC
(over-expression)

β-PIX knockdowned C-MSC injection
MPGR images
7 days after injection vehicle C-MSC injection
MPGR images
7 days after injection vehicle ALS-MSC injection

MPGR images
7 days after injection

β-PIX over-expressed ALS-MSC injection

MPGR images
7 days after injection

Fig. 8

|        | C-MSC | ALS-MSC | UCB-MSC | hUC-MSC | Vehicle C-MSC | Vehicle ALS-MSC | β-PIX knockdowned C-MSC | β-PIX overexpressed ALS-MSC |
|--------|-------|---------|---------|---------|---------------|-----------------|-------------------------|------------------------------|
| CD45   | -     | -       | -       | -       | -             | -               | -                       | -                            |
| CD34   | -     | -       | -       | -       | -             | -               | -                       | -                            |
| CD29   | +     | +       | +       | +       | +             | +               | +                       | +                            |
| CD73   | +     | +       | +       | +       | +             | +               | +                       | +                            |
| CD105  | +     | +       | +       | +       | +             | +               | +                       | +                            |
| CD44   | +     | +       | +       | +       | +             | +               | +                       | +                            |
| CD49C  | +     | +       | +       | +       | +             | +               | +                       | +                            |
| CD54   | -     | -       | -       | -       | -             | -               | -                       | -                            |
| CD106  | -     | -       | -       | -       | -             | -               | -                       | -                            |
| HLA-DR | -     | -       | -       | -       | -             | -               | -                       | -                            |

COMPOSITIONS FOR IMPROVING MIGRATION POTENTIAL OF STEM CELLS

Cross-Reference to Related Applications

This application is the U.S. national stage filing under 35 U.S.C. § 371 of international application PCT/KR2010/007152, filed Oct. 19, 2010, which claims benefit of Korean Patent Application No. 10-2009-0099146, filed Oct. 19, 2009.

BACKGROUND OF THE INVENTION

1. Field of the Invention

The present invention relates to compositions for improving migration potential of stem cells

2. Background of Technique

Adult stem cells derived from different types of tissues have different differentiation capacities and functional properties which may make them more or less effective for treating individual disorders (1). Clarification of these properties for each stem cell origin is necessary for the creation of clinical guidelines to aid in the selection of the optimal stem cell origin for patient treatment.

Mesenchymal stromal cells (MSCs) can improve the recovery of cerebral ischemia either by neuronal differentiation and replacement of damaged, or by providing neuroprotection to damaged neurons after migrating to the lesion site. The key factors governing the migratory capacity of stem cells, however, are largely unknown. Autologous MSCs are generally preferred for therapeutic transplantation because they are not subject to immune rejection. However, if the differentiation or migratory capacities of autologous MSCs lacks or are compromised, a universal donor approach should be adopted as an alternative. Therefore, it had been an important subject to identify the factors involved in stem cell migration.

Throughout this application, various publications and patents are referred and citations are provided in parentheses. The disclosures of these publications and patents in their entities are hereby incorporated by references into this application in order to fully describe this invention and the state of the art to which this invention pertains.

SUMMARY OF THE INVENTION

The present inventors have made intensive studies to elevate the efficacy of stem cell therapy by improving the migration potential of implanted stem cells to the lesion site. As results, we have discovered the factor involved in migration of the stem cells.

Accordingly, it is an object of this invention to provide a composition for improving the migration potential of a stem cell.

It is another object of this invention to provide a stem cell transformed with the composition of the present invention.

It is still another object of this invention to provide a composition for treating neurological diseases comprising the stem cell of the present invention.

It is further object of this invention to provide a method for evaluating the migration potential of a stem cell.

It is still further object of this invention to provide a method for screening an adjuvant of cell therapy improving the migration potential of a stem cell to treat neurological diseases.

Other objects and advantages of the present invention will become apparent from the following detailed description together with the appended claims and drawings.

BRIEF DESCRIPTION OF THE DRAWINGS

FIG. 1 represents the migratory capacity of MSCs depends on their origin.

FIG. 8 represents the result of the evaluation of surface marker expression of ALS-MSCs, UCB-MSCs, hUC-MSCs, and C-MSCs. The cells were characterized by staining with the following anti-human antibodies: CD45-phycoerythrin (PE), CD44-fluorescein isothiocyanate (FITC) (DakoCytomation, Denmark), CD73-PE (BD Pharmingen, CA, USA), CD34-PE, CD29-FITC, CD49C-PE, CD54-FITC, CD105-FITC, CD106-FITC, HLA-DR-FITC, and PE- and FITC-conjugated isotype controls (Serotec, UK). After staining, cells were analyzed using flow cytometry (Calibur, Calif., USA).1 On flow cytometric analysis of surface marker expression, ALS-MSCs, UCB-MSCs, hUC-MSCs, and C-MSCs commonly demonstrate a CD45-CD34-CD29+CD73+CD105+CD44+HLA-DR-phenotype. These surface markers are not different in β-PIX knockdowned C-MSCs and β-PIX overexpressed ALS-MSCs.

DETAILED DESCRIPTION OF THE INVENTION

Figure 1A:
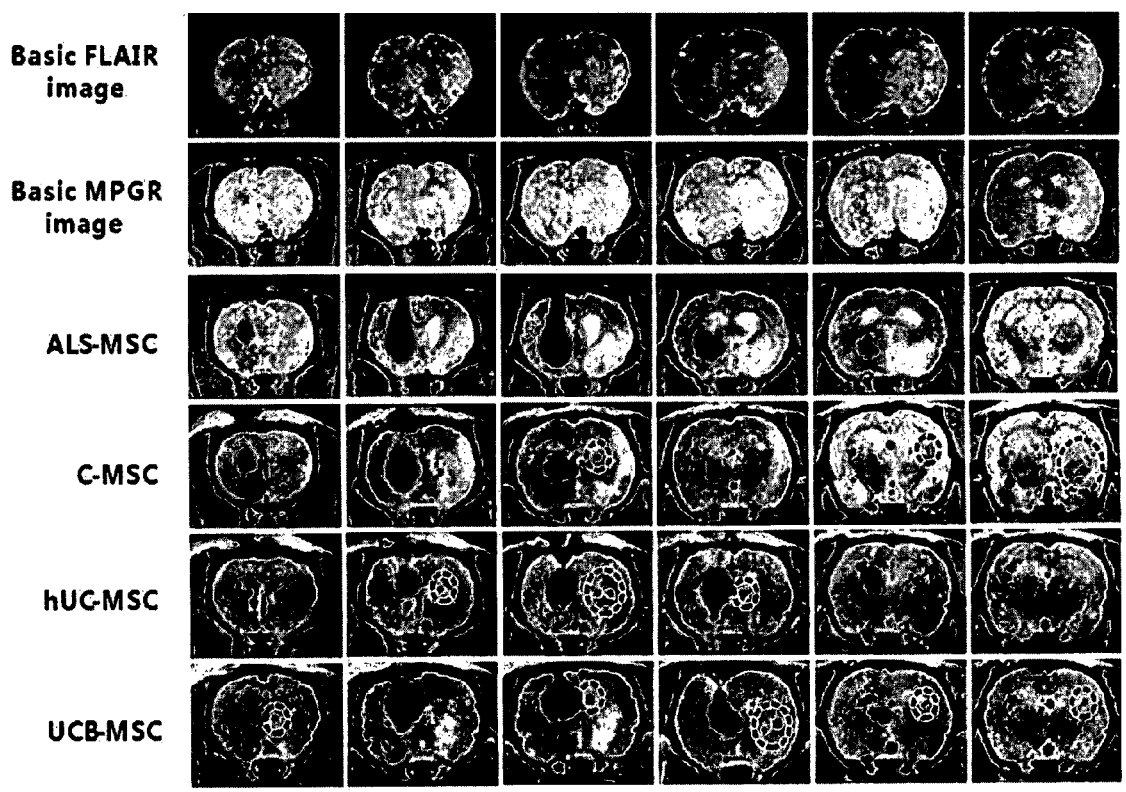
FIG. 1a shows the migratory activity of Ferumoxides-labeled mesenchymal stromal cells (MSCs) from various origins, including amyotrophic lateral sclerosis patient-derived MSC (ALSMSC), C-MSC (purchased from Cambrex), human umbilical cord-derived MSC (hUC-MSC), and umbilical cord blood-derived MSC (UCB-MSC) in the ischemic stroke model of rat brain by in vivo MR imaging. MR imaging shows that C-MSC, hUC-MSC, and UCB-MSC, which were implanted into the contralateral sides of ischemia damaged brains, migrated to the lesion site, but ALS-MSCs did not.

In one aspect of this invention, there is provided a composition for improving the migration potential of a stem cell, which comprises as an active ingredient a gene delivery system comprising a nucleotide encoding β-PIX having the amino acid sequence of SEQ ID NO:2.

In another aspect of this invention, there is provided a method for improving the migration potential of a stem cell, comprising contacting to the stem cell a gene delivery system comprising a nucleotide sequence encoding β-PIX having the amino acid sequence of SEQ ID NO:2.

The present inventors have made intensive studies to elevate the efficacy of stem cell therapy by improving the migration potential of implanted stem cells to the lesion site. As results, we have discovered that β-PIX is a crucial factor involved in migration of stem cells.

The term "gene delivery system" as used herein, refers to any forms of carriers that harbor and transport exogenous nucleic acid molecules to a target cell or tissue. As used herein, "delivery" is used interchangeably with "transduction". At the level of tissue, the term "delivery" is used interchangeably with "spread". Therefore, the term "gene delivery system" may also be written as "gene transduction system" or "gene spread system".

The gene delivery system of this invention comprises any of gene delivery system used in gene therapy by those skilled in the art, preferably, plasmid, adenovirus (Lockett L J, et al., *Clin. Cancer Res.*, 3:2075-2080(1997)), adeno-associated virus (AAV, Lashford L S., et al., *Gene Therapy Technologies, Applications and Regulations* Ed. A. Meager, 1999), retrovirus (Gunzburg W H, et al., Retroviral vectors. *Gene Therapy Technologies, Applications and Regulations* Ed. A. Meager, 1999), lentivirus (Wang G. et al., *J. Clin. Invest.* 104(11):R55-62(1999)), herpes simplex virus (Chamber R., et al., *Proc. Natl. Acad. Sci USA,* 92:1411-1415(1995)), vaccinia virus (Puhlmann M. et al., *Human Gene Therapy,* 10:649-657 (1999)) liposome ((Methods in Molecular Biology, Vol 199, S. C. Basu and M. Basu (Eds.), Human Press 2002)) or niosome. Most preferably, the gene delivery system of this invention is constructed by incorporating the β-PIX-encoding nucleotide sequence to lentiviruses. The Lentivirus is a type of retroviruses and enables transported genes to be expressed for long by integration with the stem cell genome. Furthermore, it may be infected to the fully differentiated cells as well as dividing cells.

To prepare the gene delivery system of the present invention, it is preferred that the β-PIX-encoding nucleotide sequence is inserted into an appropriate expression construct. Preferably, the β-PIX-encoding nucleotide sequence is operatively linked to a promoter in the expression construct. The term "operatively linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence.

According to the present invention, the promoter linked to the β-PIX gene, without limitation, is operable in, preferably, animal, more preferably, mammalian cells, to control transcription of the β-PIX gene. The promoter includes the promoters derived from the genome of mammalian cells or from mammalian viruses, for example, CMV (cytomegalovirus) promoter, the adenovirus late promoter, the vaccinia virus 7.5K promoter, SV40 promoter, HSV tk promoter, RSV promoter, EF1 alpha promoter, metallothionein promoter, beta-actin promoter, human IL-2 gene promoter, human IFN gene promoter, human IL-4 gene promoter, human lymphotoxin gene promoter and human GM-CSF gene promoter. Most preferably, the promoter is CMV promoter.

According to a preferred embodiment of the present invention, the polyadenylation sequence linked to the β-PIX gene comprises, but not limited to, bovine growth hormone terminator (Gimmi, E. R., et al., *Nucleic Acids Res.,* 17:6983-6998 (1989)), SV40-derived polyadenylation sequence (Schek, N., et al., *Mol. Cell. Biol.,* 12:5386-5393(1992)), HIV-1 polyA (Klasens, B. I. F., et al., *Nucleic Acids Res.,* 26:1870-1876 (1998)), β-globin polyA (Gil, A., et al., *Cell,* 49:399-406 (1987)), or poliomavirus polyA (Batt, D. B. and G. G. Carmichael, *Mol. Cell. Biol.,* 15:4783-4790(1995)).

The term "migration potential" as used herein, refers to the migratory ability of therapeutic cells to migrate to lesion sites.

According to the present invention, the amino acid sequence of SEQ ID NO:2 encoded by the β-PIX gene is very useful for improving neurological function by cell therapy through enhancing the migration potential of stem cells to lesion sites.

According to a preferred embodiment, the nucleotide sequence of this invention comprises a nucleotide of SEQ ID NO:1.

The nucleotide sequence of SEQ ID NO:1 used in the present invention is the β-PIX gene. Little has been known about biological functions of the β-PIX gene in stem cell biology. Instead, it has established functions in T cell chemotaxis across reactive barriers (3), cancer cell migration (4), and neurite outgrowth (5).

The present invention may be applied to any of stem cells including, but not limited to, embryonic stem cells, adult stem cells, induced pluripotent stem cells, embryonic germ cells, embryonic carcinoma cells, preferably, multipotent adult stem cells, and more preferably, a mesenchymal stem cell (MSC).

In the present invention, the stem cell is contacted to the gene delivery system comprising a nucleotide sequence encoding β-PIX having the amino acid sequence of SEQ ID NO:2, such that the migration potential of the stem cell is dramatically increased.

The contacting of stem cells to the gene delivery system is to transfect stem cells with the gene delivery system. The transfection may be performed in accordance with conventional techniques known to those skilled in the art. For example, stem cells may be incubated in a media for a sufficient period of time with suitable viral vectors carrying the β-PIX gene. The media for stem cells includes, but not limited to, Eagles's MEM (Eagle's minimum essential medium, Eagle, H. Science 130:432(1959)), α-MEM (Stanner, C. P. et al., Nat. New Biol. 230:52(1971)), Iscove's MEM (Iscove, N. et al., J. Exp. Med. 147:923(1978)), 199 medium (Morgan et al., Proc. Soc. Exp. Bio. Med., 73:1(1950)), CMRL 1066, RPMI 1640 (Moore et al., J. Amer. Med. Assoc. 199:519 (1967)), F12 (Ham, Proc. Natl. Acad. Sci. USA 53:288(1965)), F10 (Ham, R. G. Exp. Cell Res. 29:515(1963)), DMEM (Dulbecco's modification of Eagle's medium, Dulbecco, R. et al., Virology 8:396(1959)), mixture of DMEM and F12 (Barnes, D. et al., Anal. Biochem. 102: 255(1980)), Way-mouth's MB752/1 (Waymouth, C. J. Natl. Cancer Inst. 22:1003(1959)), McCoy's 5A (McCoy, T. A., et al., Proc. Soc. Exp. Biol. Med. 100:115(1959)) and MCDB series (Ham, R. G. et al., In Vitro 14:11(1978)).

In still another aspect of this invention, there is provided a stem cell transformed with the composition of the present invention.

As the composition for improving the migration potential of stem cells and applicable stem cells are mentioned hereinabove, they are omitted herein to avoid undue redundancy.

In still another aspect of this invention, there is provided a composition for treating neurological diseases comprising the stem cell of the present invention.

The composition of this invention may be provided as a pharmaceutical composition. The pharmaceutical composition of this invention includes a pharmaceutically acceptable carrier besides the active ingredient compound. The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methyl cellulose, methylhydroxy benzoate, propylhydroxy benzoate, talc, magnesium stearate and mineral oils. The pharmaceutical composition according to the present invention may further include a lubricant, a humectant, a sweetener, a flavoring agent, an emulsifier, a suspending agent and a preservative. Details of suitable pharmaceutically acceptable carriers and formulations can be found in Remington's Pharmaceutical Sciences (19th ed., 1995).

The pharmaceutical composition according to the present invention may be administered via the routes used commonly in gene therapy and preferably, administered parenterally, i.e., by intravenous, intraperitoneal, intramuscular, subcutaneous, or local administration. For example, the pharmaceutical composition may be administered intrathecally or intracerebroventricularly.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition and physicians of ordinary skill in the art can determine an effective amount of the pharmaceutical composition for desired treatment. Generally, a daily dosage of the pharmaceutical composition of the present invention comprises $1 \times 10^2$-$1 \times 10^{10}$ cells.

According to the conventional techniques known to those skilled in the art, the pharmaceutical composition of the present invention may be formulated with pharmaceutically acceptable carrier and/or vehicle as described above, finally providing several forms a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

The diseases treated by the composition of the present invention include any of neurological diseases caused by pathological or physical demage of nervous tissues, and preferably, Parkinson's disease, Alzheimer's disease, multiple sclerosis, amyotrophic lateral sclerosis (ALS), cerebral ischemia, cerebral hemorrhage, spinal cord injury, motor neuron disease, demyelinating disease, Huntington's disease, and more preferably, ischemic stroke.

In still another aspect of this invention, there is provided a method for evaluating the migration potential of a stem cell, comprising measuring the expression level of the nucleotide sequence of SEQ ID NO:1 in a biological sample.

The term "biological sample" as used herein refers to materials containing stem cells with biological activities to be analyzed.

The measurement of the expression level of the nucleotide of SEQ ID NO:1 may be performed by any of methods for evaluating the gene expression level generally known to those skilled in the art. For example, it may be performed through measuring mRNA level transcribed by DNA molecules, or measuring protein level translated by the mRNA.

The measurement of mRNA expression level may be carried out by amplification reaction using mRNA in the sample as template, and primers binding to mRNA or cDNA. For obtaining mRNA molecules, total RNA is isolated from samples. The isolation of total RNA may be performed by various methods (Sambrook, J. et al., Molecular Cloning. A Laboratory Manual, 3rd ed. Cold Spring Harbor Press (2001); Tesniere, C. et al., *Plant Mol. Biol. Rep.,* 9:242 (1991); Ausubel, F. M. et al., Current Protocols in Molecular Biology, John Willey & Sons (1987); and Chomczynski, P. et al., *Anal. Biochem.* 162:156 (1987)). For example, total RNA in cells may be isolated using Trizol. Afterwards, cDNA molecules are synthesized using mRNA molecules isolated and then amplified. Since total RNA molecules used in the present invention are isolated from human samples, mRNA molecules have poly-A tails and converted to cDNA by use of dT primer and reverse transcriptase (*PNAS USA,* 85:8998(1988); Libert F, et al., *Science,* 244:569(1989); and Sambrook, J. et al., Molecular Cloning. *A Laboratory Manual,* 3rd ed. Cold Spring Harbor Press (2001)). cDNA molecules synthesized are then amplified by amplification reactions.

A variety of DNA polymerases can be used in the extension step of the present methods, which includes "Klenow" fragment of *E. coli* DNA polymerase I, a thermostable DNA polymerase, and bacteriophage T7 DNA polymerase. Preferably, the polymerase is a thermostable DNA polymerase which may be obtained from a variety of bacterial species, including *Thermus aquaticus* (Taq), *Thermus thermophilus* (Tth), *Thermus filiformis*, *Thermis flavus*, *Thermococcus literalis*, and *Pyrococcus* sp. Most preferably, the polymerase obtained from *Pyrococcus* sp may be used, and the present inventors used Pyrobest™ DNA polymerase (TaKaRa, Japan).

When a polymerization reaction is being conducted, it is preferable to provide the components required for such reaction in excess in the reaction vessel. Excess in reference to components of the extension reaction refers to an amount of each component such that the ability to achieve the desired extension is not substantially limited by the concentration of that component. It is desirable to provide to the reaction mixture an amount of required cofactors such $Mg^{2+}$, dATP, dCTP, dGTP, and dTTP in sufficient quantity to support the degree of the extension desired. All of the enzymes used in polymerization reaction may be in active state at equivalent reaction conditions. In fact, buffers give the optimal reaction conditions to all enzymes. Therefore, the polymerization process of the present invention can be performed in a single reactant without change of condition such as addition of other reactants.

Annealing or hybridization in the present invention is performed under stringent conditions that allow for specific binding between the primer and the target nucleotide sequence. Such stringent conditions for annealing will be sequence-dependent and varied depending on environmental parameters.

Amplified cDNA of the nucleotide of SEQ ID NO:1 is analyzed by suitable methods to measure the expression level. For example, the resulting products are separated by gel electrophoresis and the band patterns are analyzed.

The analysis for evaluating the expression amounts of β-PIX protein may be conducted in accordance with immunoassay methods known to one skilled in the art. The immunoassay format includes, but is not limited to, radioimmunoassay, radioimmuno-precipitation, immunoprecipitation, enzyme-linked immunosorbent assay (ELISA), capture-ELISA, inhibition or competition assay, sandwich assay, flow cytometry assay, immunofluorescence staining assay and immunoaffinity assay.

The immunoassay or immunostaining procedures can be found in *Enzyme Immunoassay*, E. T. Maggio, ed., CRC Press, Boca Raton, Fla., 1980; Gaastra, W., Enzyme-linked immunosorbent assay (ELISA), in *Methods in Molecular Biology*, Vol. 1, Walker, J. M. ed., Humana Press, NJ, 1984; and Ed Harlow and David Lane, *Using Antibodies*, A Laboratory Manual, Cold Spring Harbor Laboratory Press, 1999.

For example, according to the radioimmunoassay method, the radioisotope (e.g., $C^{14}$, $I^{125}$, $P^{32}$ and $S^{35}$) labeled antibody may be used to detect the β-PIX protein.

According to the ELISA method, the specific example of the present method may further comprise the steps of: (i) coating a surface of a solid substrate with a cell lysate of interest; (ii) incubating the cell lysate to be analyzed with β-PIX protein as a primary antibody; (iii) incubating the resultant of step (ii) with a secondary antibody conjugated to an enzyme; and (iv) measuring the activity of the enzyme.

The solid substrate coated with the primary antibody is a hydrocarbon polymer (e.g., polystyrene and polypropylene), a glass, a metal or a gel, and most preferably, a microtiter plate.

The secondary antibody conjugated to an enzyme includes, but is not limited to, an enzyme catalyzing colorimetric, fluorometric, luminescence or infra-red reactions, for example, alkaline phosphatase, β-galactosidase, horseradish peroxidase, luciferase and cytochrome $P_{450}$. Where using alkaline phosphatase, bromochloroindolylphosphate (BCIP), nitro blue tetrazolium (NBT) and ECF (enhanced chemifluorescence) may be used as a substrate; in the case of using horseradish peroxidase, chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine, Pierce), HYR (p-phenylenediamine-HCl and pyrocatechol), TMB (3,3,5,5-tetramethylbenzidine), ABTS (2,2'-Azine-di[3-ethylbenzthiazoline sulfonate]), o-phenyldiamine (OPD) and naphtol/pyronin, glucose oxidase and tNBT (nitroblue tetrazolium) and m-PMS (phenzaine methosulfate) may be used as a substrate.

According to the capture-ELISA method, the specific example of the present method may comprise the steps of: (i) coating a surface of a solid substrate with an antibody of the β-PIX protein as a capturing antibody; (ii) incubating the capturing antibody with a cell sample; (iii) incubating the resultant of step (ii) with a detecting antibody having a fluorescent label which reacts with the β-PIX protein specifically; and (iv) measuring the signal generated from the label.

The detecting antibody includes a substance generating a detectable signal. The signal-generating substance bound to antibody includes, but is not limited to, chemical (e.g., biotin), enzyme (alkaline phosphatase, β-galactosidase, horseradish peroxidase and Cytochrome $P_{450}$), radio-isotope (e.g., $C^{14}$, $I^{125}$, $P^{32}$ and $S^{35}$), fluorescent (e.g., fluoresin), luminescent, chemiluminescent and FRET (fluorescence resonance energy transfer) substances. Various methods for labels and labelings are described in Ed Harlow and David Lane, *Using Antibodies: A Laboratory Manual*, Cold Spring Harbor Laboratory Press, 1999.

The analysis for measuring the activity or the signal of final enzyme in the ELISA and capture-ELISA method may be carried out by various methods known to those skilled in the art. The signal detection permits to a quantitative or qualitative analysis of the β-PIX protein. For example, the signal of each biotin- and luciferase-labeled protein may be feasibly detected using streptavidin and luciferin.

The migration potential of a stem cell may be predicted by analyzing the final strength of the signal obtained by above-mentioned immunoassay processes.

In addition, western blot analysis or immunocellularchemical assay with β-PIX specific antibodies may also be performed. Concretely, transformed cells are incubated with anti-β-PIX monoclonal antibodies and then incubated with secondary antibodies conjugated with labels such as tetramethylrhoodamine isothiocyanate (TRITC). Thereafter, the intensity of label detection is compared with negative controls to evaluate the expression level of β-PIX.

If the expression level of the nucleotide of SEQ ID NO:1 in the stem cells to be analyzed is measured to be lower than normal stem cells, they are determined to lack the migration potential (or cell therapeutic efficacy)

In still another aspect of this invention, there is provided a method for screening an adjuvant for cell therapy improving the migration potential of a stem cell to treat neurological diseases, comprising the steps of:

(a) contacting a test substance to a cell comprising the nucleotide sequence of SEQ ID NO:1; and (b) measuring the expression level of the nucleotide of SEQ ID NO:1, wherein when the expression level of the nucleotide of SEQ ID NO:1 is increased, the test substance is determined the adjuvant for cell therapy improving the migration potential of the stem cell to treat neurological diseases.

According to the present method, the cells containing the nucleotide of SEQ ID NO:1 are first contacted to test substances to be analyzed. Preferably, the cells of the present method are human stem cells, and most preferably, human mesenchymal stem cells. The term "substance" used herein in conjunction with the present screening method refers to a material to be tested in the present method for analyzing its influence on the expression level of the nucleotide of SEQ ID NO:1. The substance includes chemical compounds, peptides, antibody proteins, nucleotides, antisense-RNA, siRNA (small interference RNA) and extract of natural source, but not limited to.

Afterwards, the expression level of the nucleotide sequence of SEQ ID NO:1 is measured. Where the expression level of the nucleotide sequence of SEQ ID NO:1 is measured to be increased, the substance is determined the adjuvant for cell therapy improving the migration potential of a stem cell to treat neurological diseases.

The features and advantages of the present invention will be summarized as follows:

(a) The present invention provides a composition for improving the migration potential of a stem cell, a method for evaluating the migration potential of a stem cell and a method for screening an adjuvant for cell therapy improving the migration potential of a stem cell.

(b) The present invention may be effectively used for enhancing the efficacy of neurological disease-treatment by inducing therapeutic stem cells to migrate efficiently to the lesion site.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods
1. Animal Preparation and Ischemic Surgery.

All animal procedures were performed in accordance with the Hanyang University guidelines for the care and use of laboratory animals and were approved by the Institutional Animal Care and Use Committee (IACUC) of Hanyang University. Sprague-Dawley (SD) rats, weighing 210 to 245 g, were purchased from Biogenomics Inc. (Seoul, Korea).

After periods of adaptation and pretraining for behavioral tests, the left middle cerebral arteries (MCA) of 95 SD rats weighing 295 to 360 g were occluded for two hours using the intraluminal filament technique described in our previous study (1, 2). Throughout and following the surgery, rats were deeply anesthetized by intraperitoneal injection of tiletamine (25 mg/kg) and zolazepam (25 mg/kg, Zoletil, Yuhan Corp., Seoul, Korea) together with xylazine (10 mg/kg, Rompun, Bayer, Frankfurt, Germany) and body temperature was maintained at 36.6±0.5° C. with a thermistor-controlled heating pad. Physiological variables (pH, $pCO_2$, $pO_2$ and hematocrit) were measured in 0.1 ml aliquots of arterial blood obtained from a right femoral catheter using a blood-analysis system (International Technidyne, NJ, USA). Arterial pressure was monitored from the arterial catheter with a strain-gauge transducer (LIFE KIT DX-360; Nihon Kohden, Tokyo, Japan) and amplifier (MacLab Bridge Amplifier, ADInstruments Pty Ltd., Castle Hill, Australia). Phasic pressure, mean arterial pressure (MAP), and heart rate (HR) were recorded at a sampling rate of 200/s using a data acquisition system and laboratory computer (MacLab 8 analog-to-digital converter and Macintosh Computer). For the cerebral blood flow (CBF) study, a wire-type probe (0.3 mm diameter; Unique Medical, Tokyo, Japan) connected to a Laser Doppler flow meter (ALF21; Advance, Tokyo, Japan) was inserted 6 mm through a small burr hole placed 2 mm lateral to the bregma, such that the probe lay against the dural surface overlying the frontal cortex. Measurements were taken at a depth of 6 mm from the cortex to evaluate the deep ischemic core regions (caudate and putamen of the affected hemisphere).

After a 2-h occlusion, reperfusion was performed as described in our previous reports (1, 3).

A sham surgery was performed in additional 10 rats by introducing and immediately withdrawing a thread into the left common carotid artery. Other procedures in the sham group were identical to those used in the ischemic surgery.

2. Labeling of MSCs with Feridex and Protamine Sulfate.

The commercially available Feridex IV (TAEJOON Pharmaceutical Co., Ltd., Seoul, Korea Mfd by Advanded Managnetics, Inc. Combridge, Mass., USA)) has a total iron content of 11.2 mg/mL (11.2 iron μg/μL). Protamine sulfate (Sigma, USA) was prepared as a fresh stock solution of 1 mg/mL in distilled water at the time of use. Feridex IV at a concentration of 25 μg/mL was put into a tube containing serum-free DMEM medium (Gibco invitrogen, Carlsbad, Calif., USA) containing 100 unit/ml penicillin and 100 mg/ml streptomycin. Protamine sulfate was then added to the solution at 1 ug/ml concentrations. The solution (FE-Pro complexes) containing feridex IV and protamine sulfate was mixed for 60 minutes. And then, the solution was added to the adherent hMSC cell culture. FE-Pro complexes were added directly to the cells, incubated for 2 hours, and then an equal volume of the complete medium was added to the cells. The cell was then incubated overnight.

3. MSCs Grafting in Ischemic Stroke Model Rats.

To examine whether the migratory activity of implanted MSCs differs according to their origin, 4 kinds of MSCs such as ALS-MSCs from ALS patients (IRB-No), C-MSCs purchased from Cambrex, UCB-MSCs from umbilical cord blood (IRB-No), and hUC-MSCs from the endothelial/subendothelial layer of human umbilical cord (IRB-No) were injected into each 18 SD rats using stereotaxic surgery (ALS-MSC, C-MSC, UCB-MSC, and hUC-MSC groups, respectively) two weeks after intraluminal left MCA occlusion (MCAo). An equivalent volume of PBS was similarly injected into the remaining 18 rats (PBS group). All these groups were not statistically different in body weight (from 317.3±22.0 g to 324.3±14.1 g) or motor and behavioral deficit score (from 6.6±0.7 to 7.0±0.8) just before the implantation. The animals were anesthetized with pentobarbital sodium (50 mg/kg, IP). We implanted 5 μl suspensions of $6 \times 10^5$ each kind of MSCs, and PBS in one site contralateral (Site: AP=+0.7, R=+2, V=−5.5) to the lesion. The suspensions were delivered in 2 min, and the syringe was then left in place for an additional 2 min. For the control group, 5 μl of PBS was used. The rats in both groups received daily immunosuppression with cyclosporine A (10 mg/kg body weight, subcutaneously; Sandoz, Switzerland) from two days before cell transplantation until the end of the study.

4. Behavioral Tests of Ischemic Stroke Model Rats.

All animals were trained for neurobehavioral assessment for seven days before MCAO. The neurologic examination was performed daily to assess a neurologic deficit score (NDS) comprised of consciousness (0, normal; 1, restless; 2, lethargic; 3, stuporous; 4, death), gait (0, normal; 1, paw adduction; 2, unbalanced walking; 3, circling; 4, unable to stand; 5, no movement), limb tone (0, normal; 1, spastic; 2, flaccid), and pain reflex (0, normal; 2, hypoactive; 4, absent)

at 2 hrs and 7, 14 (just before implantation), 21, 28, and 35 days after MCAO by an investigator who was blind to the experimental groups (4).

5. In Vivo MRI Study

In MRI studies, all the rats were anesthetized with pentobarbital sodium (50 mg/kg IP) and fixed to a Taoka rat cradle. They maintained respiration without assistance. A 3-inch-diameter circular receive-only surface coil was plated under the head of each rat, with the center of the coil located at the midpoint of the midline between the ear-ear and eye-eye lines. Body temperature was kept at 37° C. with a heating pad. The temperature of the MR imaging room was controlled to roughly 27° C., and MR imaging was performed with 3T clinical instrument (Philips, Netherland) with animal coil (Shanghai Chenguang Medical TechnologiesCo., LTD, China). For the elucidation of the extent of ischemic lesion, Fluid Attenuated Inversion Recovery (FLAIR) images were obtained using the spin-echo technique (TR=11,000 ms and TE=125 ms) between the vertex of the head and the bottom of the brain. Other imaging parameters included 0.7 mm slice thickness, point resolution of 284×286 μm and number of acquisitions=1. For T2* weighted images of a rat brain with Multiplanar Gradient-Recalled (MPGR) pulse sequence, the following parameters were adopted: TR=596 ms, TE=16 ms, section thickness=0.7 mm, point resolution: 292×290 μm and number of acquisitions=1.

6. Immunohistochemistry of Human Mitochondria.

To confirm whether the low signal intensities shown the MPGR images are due to the implanted MSCs, we sacrificed three rats from the C-MSC group 35 days after the implantation. Anti-human mitochondria monoclonal antibody (1:100, Chemicon, Temecula, Calif., USA) was used as a primary antibody. Coronal sections (20 μm thickness) of the brain were prepared and incubated with one of the primary antibody for 72 hours at 4° C. The sections were washed three times for 5 min each to remove unbound antibodies and then incubated for 24 hours with the appropriate secondary antibody conjugated to TRITC. Unbound secondary antibody was removed with three rinses of 5 min each. After air-drying, coverslip was applied to the slides with Vector Shield mounting medium. As a negative control, the above procedures were repeated without primary antibodies. Cell staining was not observed in the negative control.

A laser-scanning confocal microscopy system mounted onto a LEICA DMIRE2 microscope (Germany) was used. For immunofluorescence-labeled slides, red (TRITC) fluorochromes on the slides were excited by the laser beam at 557-nm, and emissions were acquired sequentially with a photomultiplier tube through 576-nm emission filters, respectively. The implanted stem cells were stained with antibody for human mitochondria.

7. Production and Propagation of the Recombinant Lentivirus.

To confirm the role of β-PIX in the migration of stem cells in vivo, we used lentiviral DNAs bearing the β-PIX specific shRNA or cDNA. The lentiviral DNA containing the shRNA were purchased from Open biosystems with Trans-Lentivire™ GIPZ packaging System (OpenBiosystem, USA). The viral stocks were produced following the manufacturer's instructions. For β-PIX gene over-expression, the β-PIX and GFP cDNAs were subcloned into the pLenti6/V5-D-TOPO (Invitrogen, USA) and confirmed by sequencing. The recombinant β-PIX- or GFP-Lentivirus was produced following the manufacturer's instructions (Invitrogen, USA) with minor modification. To determine viral concentration of the viral stocks, the viral supernatants were serial diluted and transduced into hBM-MSC or HT1080 cells with 6 μg/ml Polybrene (Sigma, USA) and then cells were selected by 6 μg/ml Blasticidin (Invitrogen, USA) (M. Kimura et al., 1994) for 10 days. The remaining cells were stained with crystal violet and colonies were counted under the microscopy. For the lentivirus carrying GFP gene, the virus was transduced into hBM-MSCs following the described above. GFP-transduced hBM-MSCs were growth for 3 days and fixed in 1% paraformaldehyde and the fluorescence activities are read using by FACS machine. We obtained $6 \times 10^5$ TU (transduction unit)/ml of β-PIX gene-transduced viral particals in HT1080 cell, $2 \times 10^5$ TU/ml in hBM-MSCs and $1 \times 10^5$ TU/ml of the shRNA-transduced viral particals in hBM-MSCs. To obtain the high concentration of recombinant virus, the virus-containing supernatants were harvested using ultracentrifugation at 28,000 g for 90 min and stored −80° C.

8. Lentiviral Infection.

hBM-MSCs were seeded at a density of $8 \times 10^5$ cells per 75T flasks. MSCs were exposed to 0, 2 or 5 multiplicity of infection (MOI) of the infectious viral particles containing the shRNA, GFP or β-PIX gene in 15 ml DMEM media at 37° C. for overnight and the media were removed and cells washed once with DMEM. The cells were then incubated for 4 days with normal medium, and alteration of migratory activity in β-PIX gene-modified MSCs was evaluated in vitro and in vivo condition by using the above described methods.

9. Cell Migration Assay.

Cell migration was examined by a QCM chemotaxis (8 μm pore size) 96-well migration assay (Chemicon, USA). Briefly, the migration chambers were coated with 50 μl of HA (5 mg/ml) and air-dried overnight. $5 \times 10^4$ MSCs in 100 μl serum-free medium were seeded in the migration chamber. The lower chamber contained 150 μl of serum-free medium containing 10% bovine serum albumin. The plates were incubated at 37° C. in 5% $CO_2$ for 24 hrs. After incubation, MSCs suspended in media in the migration chamber were gently removed by flipping out the medium. The cells adhering to the top side of the membrane were removed by scratching with a cotton applicator, and the migration chamber plate was then placed onto a new 96-well feeder tray containing 150 μl of prewarmed cell detachment solution in the wells. After 30 minutes of incubation at 37° C., 50 μl of a lysis buffer/dye solution was added to the feeder tray and incubated 15 minutes at room temperature. The mixture (150 μl) was then transferred to a new 96-well plate and the plate was read with a fluorescence plate reader using a 480/520-nm filter set (HTS 7000 Bioassay reader), which was performed according to the manufacturer's instructions (5).

10. Real Time PCR and Reverse Transcription-Polymerase Chain Reaction (RT-PCR).

To investigate the difference of the level of mRNA for β-PIX, four kinds of MSCs such as ALS-MSCs, C-MSCs, UCB-MSCs, and hUC-MSCs were harvested at near confluence, and total RNAs were extracted using Trizol reagent following the manufacturer's instructions (Invitrogen, USA). 5 μg total RNA was reverse-transcribed using RevertAid™ M-MuLV reverse transcriptase (MBI Fermentas, USA), 0.2 μg random primer (Invitrogen, USA), 1 mM dNTPs, and the supplied buffer. The first strand cDNA was amplified using Taq DNA polymerase (MBI Fermentas, MD) with 5'-AAGCGCAAACCTGAACGGAA-3' (upstream) and 5'-TCACCTCAGAACTGGTCTTCA-3' (downstream) as primers for β-PIX and 5'-TGCTATCCCTGAAAGCCTCTG-3' (upstream) and 5'-AGCTGGGGTGATGAAGCTGTA-3' (downstream) primers for β-actin. For cloning human β-PIX gene, the first strand cDNA from wild type MSCs was amplified using Pyrobest™ DNA polymerase (TaKaRa, Japan) with primers 5'-CACCATGACCGATAATAGCAACAA -3'

(forward) and 5'-TCACCTCAGAACTGGTCTTCA-3' (reverse). The PCR cycling parameters were as follows: initial denaturation at 94° C. for 2 min; 30 cycles of 30 s at 94° C. for denaturation, 30 s at 55° C. for primer annealing, and 1 min at 72° C. for extension; and final extension at 72° C. for 10 min. After amplification, the PCR products were resolved by agarose gel electrophoresis. For quantification of gene transcripts, real time PCR was performed in 96-well plates, with a final volume of 20 µl/well using the SYBR Green PCR kit (Applied Biosystems, Inc., Foster City, Calif., USA). Each reaction volume contained 10 µl of SYBR Green mix (2× concentrated), 6 µl of $H_2O$, 1 µl of cDNA sample, and 3 µl of primer mix (sense and antisense primers, each 2 pmol/µl). The real time PCR cycling parameters were as follows: initial denaturation at 95° C. for 10 min; 40 cycles of 15 sec at 95° C. for denaturation, 1 min at 60° C. for primer annealing and extension. After the amplification protocol a dissociation curve was constructed by ramping the temperature from 60 to 90° C. The resulting Ct values were converted to absolute amounts of cDNA present in the sample (E-Ct) (37). To correct for differences in cDNA amounts between samples, we normalized the target PCR to the geometric mean values of PCRs on a set of reference genes.

11. Quantitative PCR Array.

Two plates of the RT2 Profiler PCR array for human tumor metastasis (PANS-028; SuperArray Bioscience Corporation, Frederick, Md., USA) were used to compare Q-PCR validated cDNA samples of normal- and ALS-MSCs. cDNA equivalent to 1 µg of total RNA was used for each plate. The cDNA was mixed with the RT2 SYBR Green/ROX Q-PCR Master Mix, and 25 µl was added to each of the wells containing different primers. The plate was run under the same conditions as described above. The outcome was normalized against the set of reference genes used for the Q-PCR. Analysis using the references genes present on the array yielded a comparable outcome.

12. Western Blotting and Immunocytochemistry.

To assess the difference of the protein level of β-PIX, western blot and immunocytochemistry were performed with a specific antibody for β-PIX (Cell signaling, USA).

First, western blot was performed with the antibody (1:1000) according to previously described procedures (28). $5×10^6$ MSCs cultured for 24 hrs were used for western blot. All figures are representative of at least five independent experiments. And then, immnucytochemistry was performed. After culture for 24 hrs, the cells were washed with PBS and fixed with 4% paraformaldehyde in PBS for 20 min at 4° C. Following several washes, the cells were permeabilized with 0.5% Triton X-100 for 20 min. After incubation in 5% BSA in PBS for one hour, the cells were reacted with anti-β-PIX monoclonal antibody (1:100) overnight at 4° C. Following incubation, the cells were washed three times for 5 min each to remove unbound antibodies and then incubated with the appropriate secondary antibody conjugated to TRITC for 20 min at room temperature. Unbound secondary antibody was removed by three rinses lasting 10 min each. The coverslip was overlaid with Vector Shield mounting medium (Vector Laboratories, CA, USA). As a negative control, the above procedures were also carried out with mouse IgG antibody (Kamiya Biomedical, WA, USA).

13. Comparison of Neurotrophic Factors.

The present inventors hypothesized that reduced β-PIX expression could decrease the secretion of neurotrophic factors that are important for the improvement of motor functions by MSCs. A total of $1×10^4$ ALS-MSCs or C-MSCs were plated in 96-well plates. After incubation for 24 hrs, each culture supernatant was divided into 200 µL triplicate samples. Vascular endothelial growth factor (VEGF), stromal cell-derived factor-1α (SDF-1α), and brain-derived neurotrophic factor (BDNF) levels were measured in the culture supernatants with BDNF, SDF-1α, and VEGF ELISA kits (R&D Systems, USA) by following the manufacturer's instructions (2). When compared with C-MSCs, concentrations of SDF-1α (A) and VEGF (B) were significantly decreased in culture supernatant of ALS-MSCs but concentration of BDNF (C) was not. The level of these neurotrophic factors is not affected by genetic modulation of β-PIX.

Results

1. Comparison of Migratory Capacity of MSCs Derived from Different Origins.

Figure 1B:
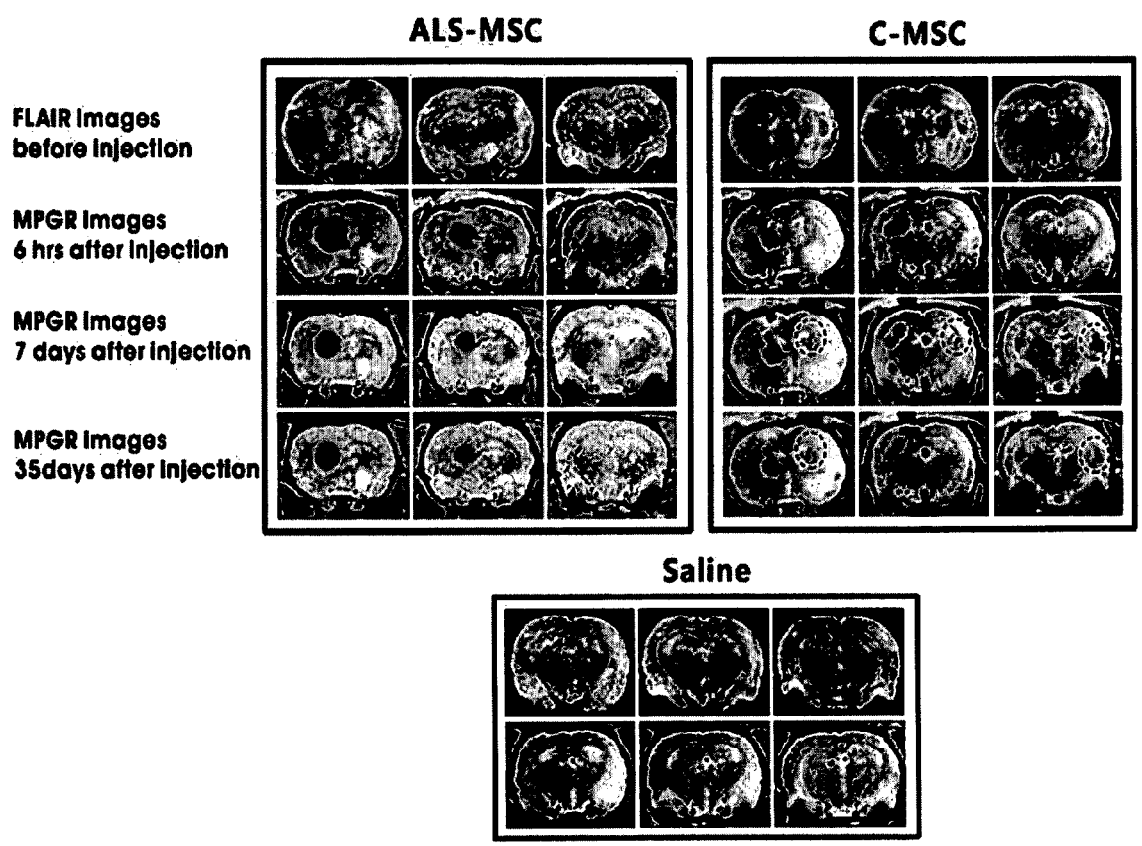
FIG. 1b shows that the ALS-MSC did not migrate 35 days after implantation.
Figure 5:
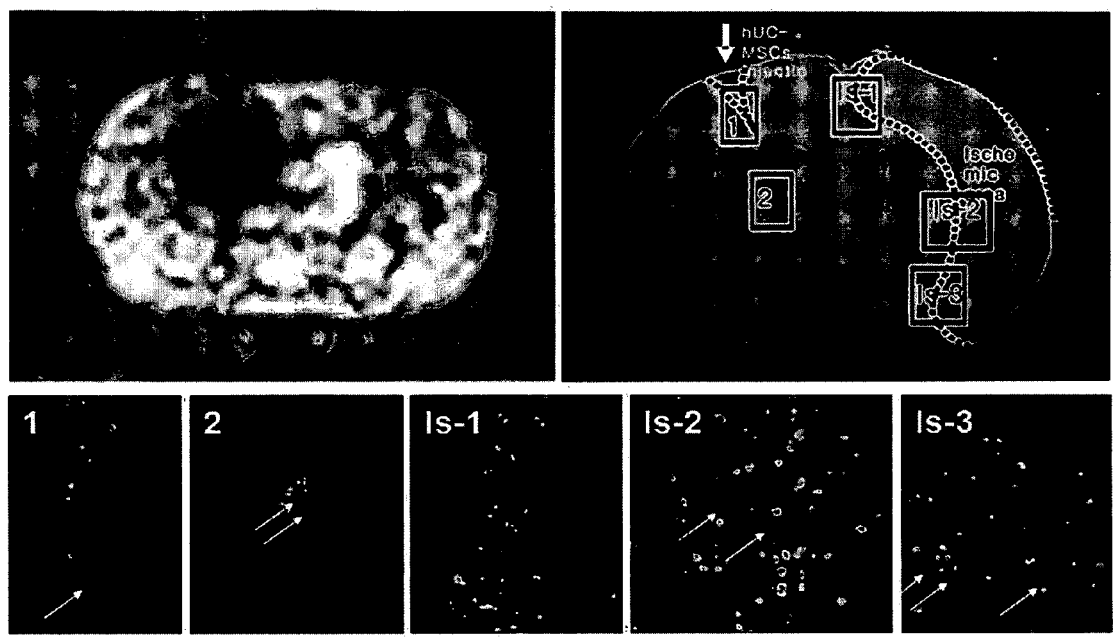
FIG. 5 represents the confirmation of migration of implanted MSCs with MR imaging and immunohistochemistry. Considering the results of the MPGR image and the immunohistochemical staining, migration of MSCs to the contralateral lesion site from the primary injection site is found as migratory spots in the MPGR image

We followed the migration of Ferumoxides-labeled MSCs in rat brains using in vivo MR imaging. MSCs were derived from different origins including amyotrophic lateral sclerosis patient bone marrow (ALS-MSC), normal human bone marrow of which MSCs were purchased from Cambrex® (C-MSC), human umbilical cord tissue (hUC-MSC), and umbilical cord blood (UCB-MSC). The path of migratory MSCs in T2*-weighted images of the ischemic rat brain can be easily tracked by observing the hypointense voxels (i.e., dark regions) (FIG. 5). Surprisingly, the ALS-MSC lacked migratory capability, while all other MSC populations migrated to the lesion sites (FIG. 1a). Out of 10 rats in each group, hypointense voxels were detected in seven rats of the C-MSC group, eight of the hUC-MSC group, nine of the UCB-MSC group, and only one of the ALS-MSC group. This negates the assumption in the field of MSC transplantation that all sources of MSCs possess migratory capacity in the brain. The migratory behaviours of ALS-MSC and C-MSCs in MSC-implanted rat brains were followed up to 35 days after transplantation and after 35 days, the ALS-MSCs did not show migratory activity compared to C-MSCs (FIG. 1b).

Figure 1C:
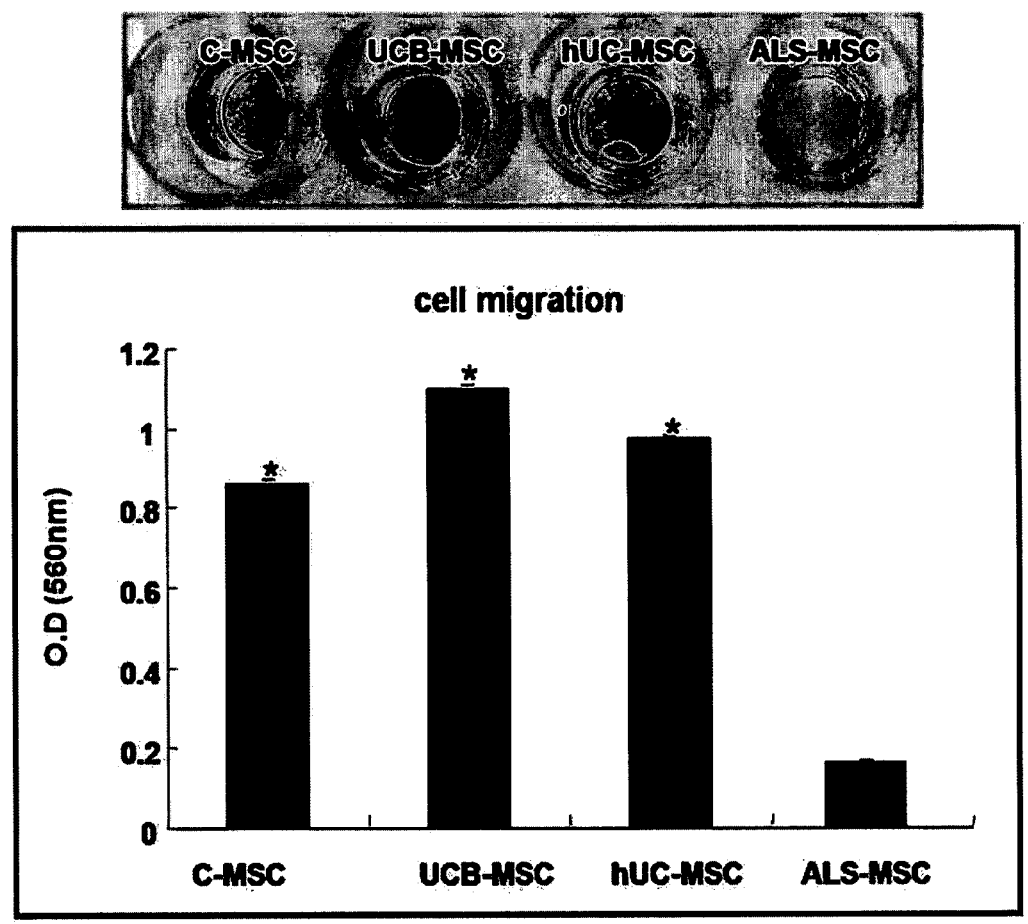
FIG. 1c shows the result of in vitro cell migration assays indicating that C-MSC, hUC-MSC, and UCB-MSC had migratory capacity, but ALS-MSCs did not.
Figure 6:
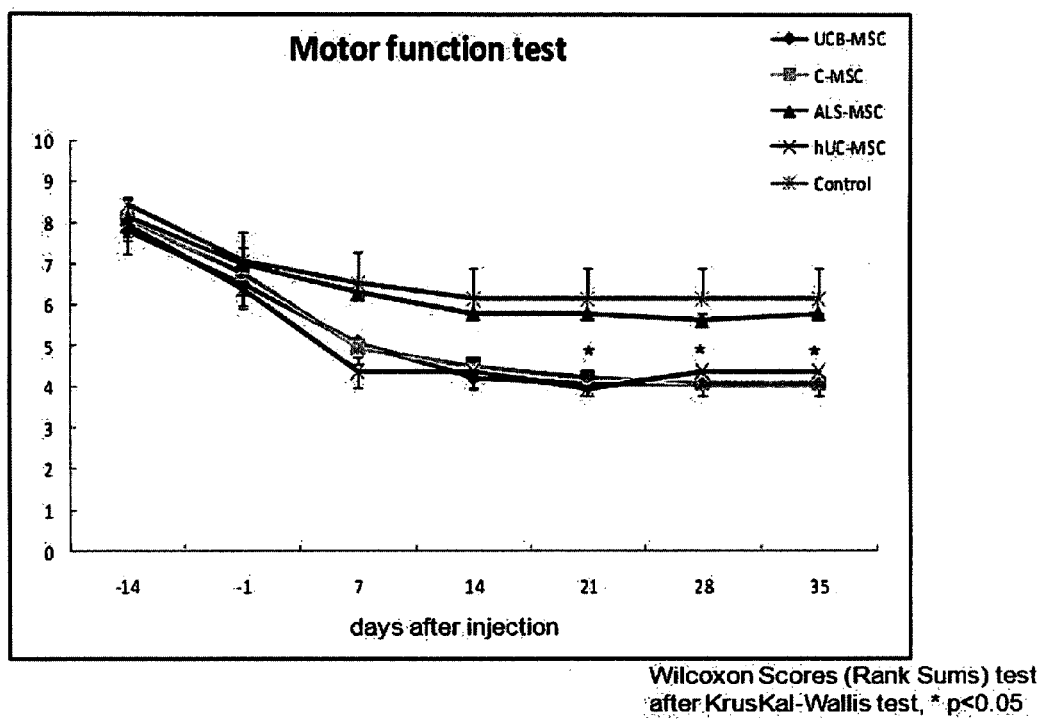
FIG. 6 represents the alteration of behavioral functions after the implantation of MSCs depending on their origin. A decrease in the neurologic deficit score (NDS) indicates an improvement in behavioral functions. As shown in this figure, there was no difference between the five groups prior to implantation, but the NDS was significantly lower in the C-MSC, hUC-MSC, and UCB-MSC groups (N=10 in each group) than in the ALS-MSC group (N=10) from 7 days after implantation although statistically significant difference was shown from 21 days after implantation. In other words, C-MSCs, hUC-MSCs, and UCB-MSCs significantly improved behavioral functions of ischemic stroke rats but ALS-MSCs did not. [*$p<0.05$ when compared with the PBS group, Wilcoxon Scores (Rank Sums) Test after Kruskal-Wallis Test].

The results of the MR studies for the in vivo migratory capacity of different MSC populations was also corroborated by in vitro transwell chemotaxis assays as shown in FIG. 1c. Moreover, the recovery of motor function of rats with ischemic stroke that were implanted with C-MSCs, hUC-MSCs, or UCB-MSCs significantly improved, while ALSMSCs failed to support motor function improvement (FIG. 6).

2. Behavioral Tests of Ischemic Stroke Model Rats.

A decrease in the neurologic deficit score (NDS) indicates an improvement in behavioral functions. As shown in FIG. 6, there was no difference between the five groups prior to implantation, but the NDS was significantly lower in the C-MSC, hUC-MSC, and UCB-MSC groups (N=10 in each group) than in the ALS-MSC group (N=10) from 7 days after implantation although statistically significant difference was shown from 21 days after implantation. In other words, C-MSCs, hUC-MSCs, and UCB-MSCs significantly improved behavioral functions of ischemic stroke rats but ALS-MSCs did not.

3. Quantitative PCR Array.

Figure 7:
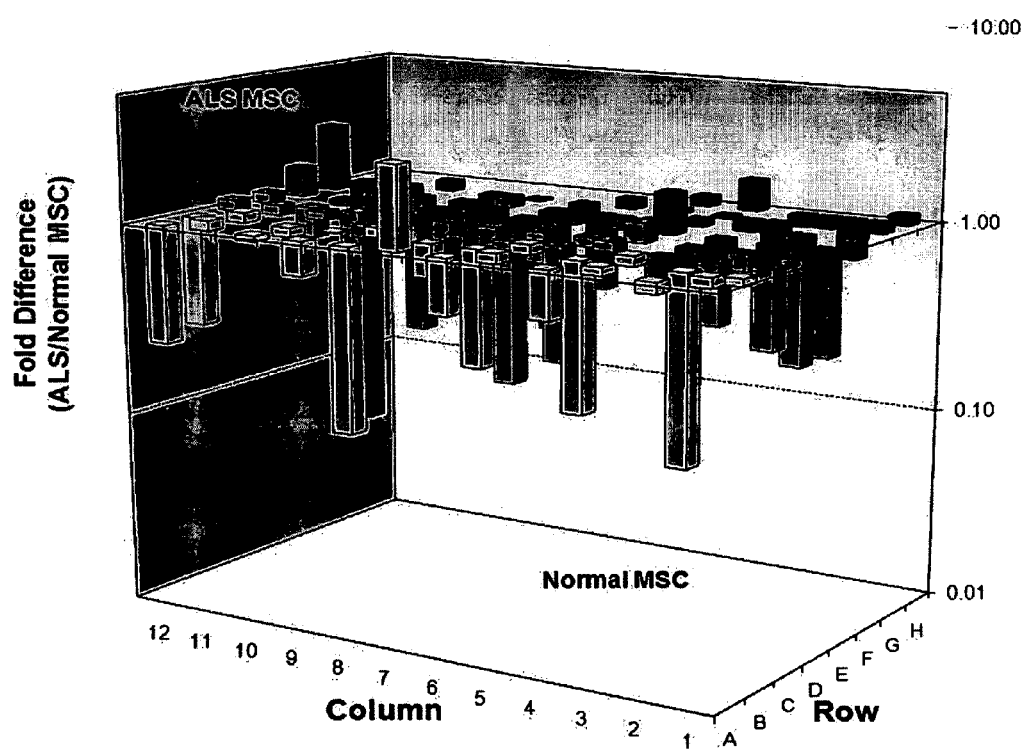
FIG. 7 represents the result of quantitative PCR assay to evaluate the difference of migration associated genes between ALS-MSCs and C-MSCs

Quantitative PCR was used to identify genes that are necessary for cancer cell migration and play a role in MSC migration to lesion sites (FIG. 7). The expression of genes such as VEGFA, CTSK, β-PIX, and MTSS1 were markedly lower in ALS-MSCs than C-MSCs (FIG. 2a). VEGFA was used as internal control because it is known to be down-regulated in ALS patients (2). The β-PIX gene expression was reduced 7.58 fold, yet has no known functions in stem cell biology. Instead, it has established functions in T cell chemotaxis across reactive barriers (3), cancer cell migration (4), and neurite outgrowth (5).

TABLE 1

Names of migration associated genes which were investigated in this study

| Unigene | GeneBank | Symbol | Description |
|---|---|---|---|
| Hs.158932 | NM_000038 | APC | Adenomatous polyposis coli |
| Hs.100426 | NM_015399 | BRMS1 | Breast cancer metastasis suppressor 1 |
| Hs.251526 | NM_006273 | CCL7 | Chemokine (C—C motif) ligand 7 |
| Hs.502328 | NM_000610 | CD44 | CD44 molecule (Indian blood group) |
| Hs.461086 | NM_004360 | CDH1 | Cadherin 1, type 1, E-cadherin (epithelial) |
| Hs.116471 | NM_001797 | CDH11 | Cadherin 11, type 2, OB-cadherin (osteoblast) |
| Hs.171054 | NM_004932 | CDH6 | Cadherin 6, type 2, K-cadherin (fetal kidney) |
| Hs.512599 | NM_000077 | CDKN2A | Cyclin-dependent kinase inhibitor 2A (melanoma, p16, inhibits CDK4) |
| Hs.162233 | NM_001273 | CHD4 | Chromodomain helicase DNA binding protein 4 |
| Hs.508716 | NM_001846 | COL4A2 | Collagen, type IV, alpha 2 |
| Hs.143212 | NM_003650 | CST7 | Cystatin F (leukocystatin) |
| Hs.208597 | NM_001328 | CTBP1 | C-terminal binding protein 1 |
| Hs.534797 | NM_001903 | CTNNA1 | Catenin (cadherin-associated protein), alpha 1, 102 kDa |
| Hs.632466 | NM_000396 | CTSK | Cathepsin K |
| Hs.716407 | NM_001912 | CTSL1 | Cathepsin L1 |
| Hs.522891 | NM_000609 | CXCL12 | Chemokine (C—X—C motif) ligand 12 (stromal cell-derived factor 1) |
| Hs.593413 | NM_003467 | CXCR4 | Chemokine (C—X—C motif) receptor 4 |
| Hs.22393 | NM_003677 | DENR | Density-regulated protein |
| Hs.523329 | NM_004442 | EPHB2 | EPH receptor B2 |
| Hs.434059 | NM_001986 | ETV4 | Ets variant 4 |
| Hs.374477 | NM_005243 | EWSR1 | Ewing sarcoma breakpoint region 1 |
| Hs.481371 | NM_005245 | FAT1 | FAT tumor suppressor homolog 1 (*Drosophila*) |
| Hs.165950 | NM_002011 | FGFR4 | Fibroblast growth factor receptor 4 |
| Hs.646917 | NM_002020 | FLT4 | Fms-related tyrosine kinase 4 |
| Hs.203717 | NM_002026 | FN1 | Fibronectin 1 |
| Hs.333418 | NM_014164 | FXYD5 | FXYD domain containing ion transport regulator 5 |
| Hs.82963 | NM_000825 | GNRH1 | Gonadotropin-releasing hormone 1 (luteinizing-releasing hormone) |
| Hs.208229 | NM_032551 | KISS1R | KISS1 receptor |
| Hs.396530 | NM_000601 | HGF | Hepatocyte growth factor (hepapoietin A; scatter factor) |
| Hs.44227 | NM_006665 | HPSE | Heparanase |
| Hs.37003 | NM_005343 | HRAS | V-Ha-ras Harvey rat sarcoma viral oncogene homolog |
| Hs.90753 | NM_006410 | HTATIP2 | HIV-1 Tat interactive protein 2, 30 kDa |
| Hs.160562 | NM_000618 | IGF1 | Insulin-like growth factor 1 (somatomedin C) |
| Hs.83077 | NM_001562 | IL18 | Interleukin 18 (interferon-gamma-inducing factor) |
| Hs.126256 | NM_000576 | IL1B | Interleukin 1, beta |
| Hs.846 | NM_001557 | IL8RB | Interleukin 8 receptor, beta |
| Hs.524484 | NM_002206 | ITGA7 | Integrin, alpha 7 |
| Hs.218040 | NM_000212 | ITGB3 | Integrin, beta 3 (platelet glycoprotein IIIa, antigen CD61) |
| Hs.527778 | NM_002231 | CD82 | CD82 molecule |
| Hs.95008 | NM_002256 | KISS1 | KiSS-1 metastasis-suppressor |
| Hs.505033 | NM_004985 | KRAS | V-Ki-ras2 Kirsten rat sarcoma viral oncogene homolog |
| Hs.449909 | NM_002295 | RPSA | Ribosomal protein SA |
| Hs.599039 | NM_006500 | MCAM | Melanoma cell adhesion molecule |
| Hs.484551 | NM_002392 | MDM2 | Mdm2 p53 binding protein homolog (mouse) |
| Hs.132966 | NM_000245 | MET | Met proto-oncogene (hepatocyte growth factor receptor) |
| Hs.444986 | NM_006838 | METAP2 | Methionyl aminopeptidase 2 |
| Hs.651869 | NM_002410 | MGAT5 | Mannosyl (alpha-1,6-)-glycoprotein beta-1,6-N-acetyl-glucosaminyltransferase |
| Hs.2258 | NM_002425 | MMP10 | Matrix metallopeptidase 10 (stromelysin 2) |
| Hs.143751 | NM_005940 | MMP11 | Matrix metallopeptidase 11 (stromelysin 3) |
| Hs.2936 | NM_002427 | MMP13 | Matrix metallopeptidase 13 (collagenase 3) |
| Hs.513617 | NM_004530 | MMP2 | Matrix metallopeptidase 2 (gelatinase A, 72 kDa gelatinase, 72 kDa type IV collagenase) |
| Hs.375129 | NM_002422 | MMP3 | Matrix metallopeptidase 3 (stromelysin 1, progelatinase) |
| Hs.2256 | NM_002423 | MMP7 | Matrix metallopeptidase 7 (matrilysin, uterine) |
| Hs.297413 | NM_004994 | MMP9 | Matrix metallopeptidase 9 (gelatinase B, 92 kDa gelatinase, 92 kDa type IV collagenase) |
| Hs.525629 | NM_004689 | MTA1 | Metastasis associated 1 |
| Hs.700429 | NM_014751 | MTSS1 | Metastasis suppressor 1 |
| Hs.202453 | NM_002467 | MYC | V-myc myelocytomatosis viral oncogene homolog (avian) |
| Hs.437922 | NM_005376 | MYCL1 | V-myc myelocytomatosis viral oncogene homolog 1, lung carcinoma derived (avian) |
| Hs.187898 | NM_000268 | NF2 | Neurofibromin 2 (merlin) |
| Hs.118638 | NM_000269 | NME1 | Non-metastatic cells 1, protein (NM23A) expressed in |
| Hs.463456 | NM_002512 | NME2 | Non-metastatic cells 2, protein (NM23B) expressed in |
| Hs.9235 | NM_005009 | NME4 | Non-metastatic cells 4, protein expressed in |
| Hs.279522 | NM_006981 | NR4A3 | Nuclear receptor subfamily 4, group A, member 3 |
| Hs.466871 | NM_002659 | PLAUR | Plasminogen activator, urokinase receptor |
| Hs.409965 | NM_002687 | PNN | Pinin, desmosome associated protein |
| Hs.500466 | NM_000314 | PTEN | Phosphatase and tensin homolog |
| Hs.408528 | NM_000321 | RB1 | Retinoblastoma 1 |
| Hs.494178 | NM_006914 | RORB | RAR-related orphan receptor B |
| Hs.436687 | NM_003011 | SET | SET nuclear oncogene |
| Hs.12253 | NM_005901 | SMAD2 | SMAD family member 2 |
| Hs.75862 | NM_005359 | SMAD4 | SMAD family member 4 |
| Hs.195659 | NM_005417 | SRC | V-src sarcoma (Schmidt-Ruppin A-2) viral oncogene homolog (avian) |
| Hs.514451 | NM_001050 | SSTR2 | Somatostatin receptor 2 |
| Hs.371720 | NM_003177 | SYK | Spleen tyrosine kinase |

TABLE 1-continued

Names of migration associated genes which were investigated in this study

| Unigene | GeneBank | Symbol | Description |
|---|---|---|---|
| Hs.475018 | NM_005650 | TCF20 | Transcription factor 20 (AR1) |
| Hs.645227 | NM_000660 | TGFB1 | Transforming growth factor, beta 1 |
| Hs.633514 | NM_003255 | TIMP2 | TIMP metallopeptidase inhibitor 2 |
| Hs.644633 | NM_000362 | TIMP3 | TIMP metallopeptidase inhibitor 3 |
| Hs.591665 | NM_003256 | TIMP4 | TIMP metallopeptidase inhibitor 4 |
| Hs.478275 | NM_003810 | TNFSF10 | Tumor necrosis factor (ligand) superfamily, member 10 |
| Hs.654481 | NM_000546 | TP53 | Tumor protein p53 |
| Hs.155942 | NM_002420 | TRPM1 | Transient receptor potential cation channel, subfamily M, member 1 |
| Hs.160411 | NM_000369 | TSHR | Thyroid stimulating hormone receptor |
| Hs.73793 | NM_003376 | VEGFA | Vascular endothelial growth factor A |
| Hs.534255 | NM_004048 | B2M | Beta-2-microglobulin |
| Hs.412707 | NM_000194 | HPRT1 | Hypoxanthine phosphoribosyltransferase 1 |
| Hs.523185 | NM_012423 | RPL13A | Ribosomal protein L13a |
| Hs.592355 | NM_002046 | GAPDH | Glyceraldehyde-3-phosphate dehydrogenase β-PIX |
| Hs.520640 | NM_001101 | ACTB | Actin, beta |
| N/A | SA_00105 | HGDC | Human Genomic DNA Contamination |
| N/A | SA_00104 | RTC | Reverse Transcription Control |
| N/A | SA_00104 | RTC | Reverse Transcription Control |
| N/A | SA_00104 | RTC | Reverse Transcription Control |
| N/A | SA_00103 | PPC | Positive PCR Control |
| N/A | SA_00103 | PPC | Positive PCR Control |
| N/A | SA_00103 | PPC | Positive PCR Control |

4. Analysis of Cell Migration According to β-PIX Expression.

Figure 3A:
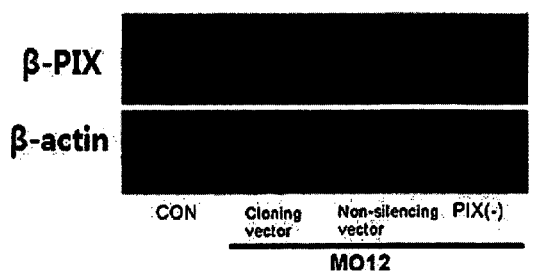
FIG. 3 represents that the alteration of β-PIX expression affects migratory capacity. Knockdown of β-PIX mRNA and protein was induced in C-MSC with shRNA (FIG. 3a). β-PIX over-expression in ALS-MSC with β-PIX-Lentivirus increased ALS-MSC migratory capacity (FIGS. 3b and 3c). β-PIX knockdown decreased C-MSC migratory capacity (FIG. 3c).
Figure 3A:
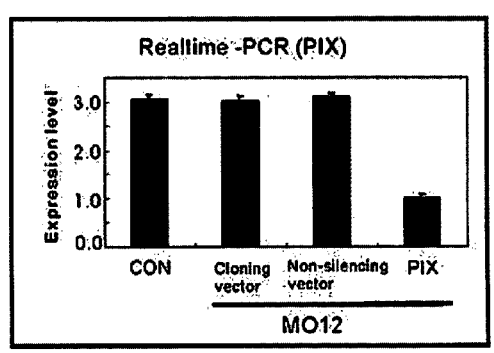
Figure 3A:
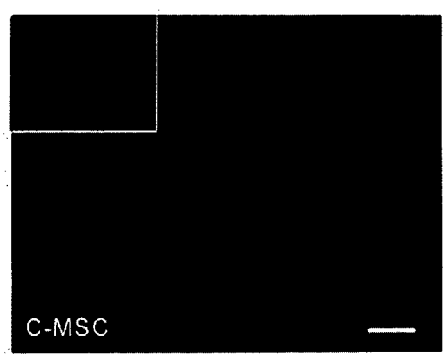
Figure 3A:
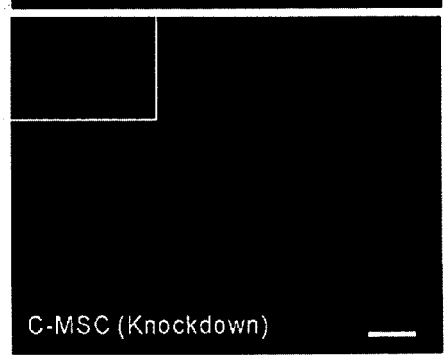
Figure 3B:
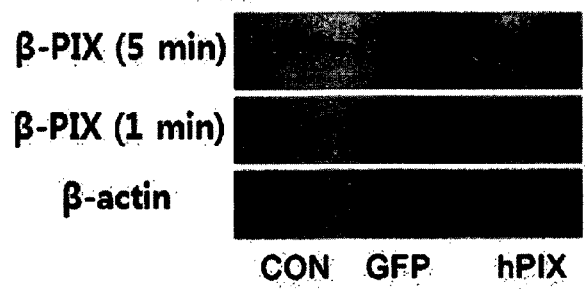
Figure 3B:
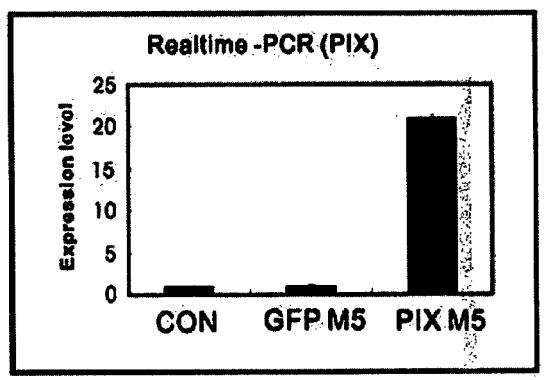
Figure 3B:
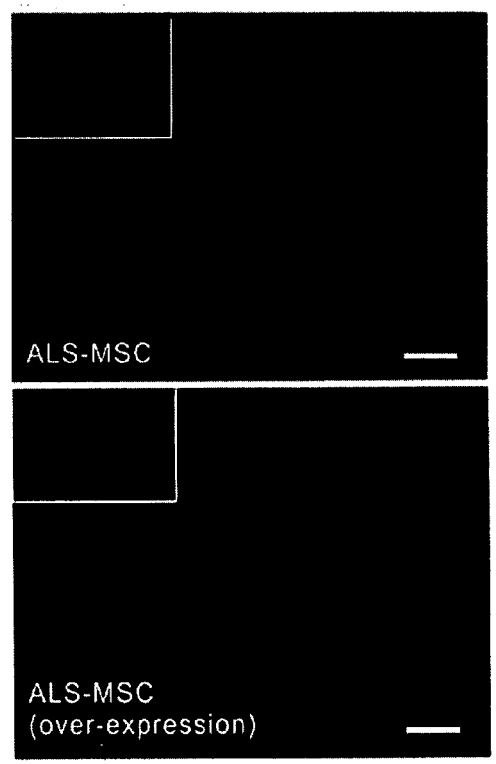
Figure 3C:
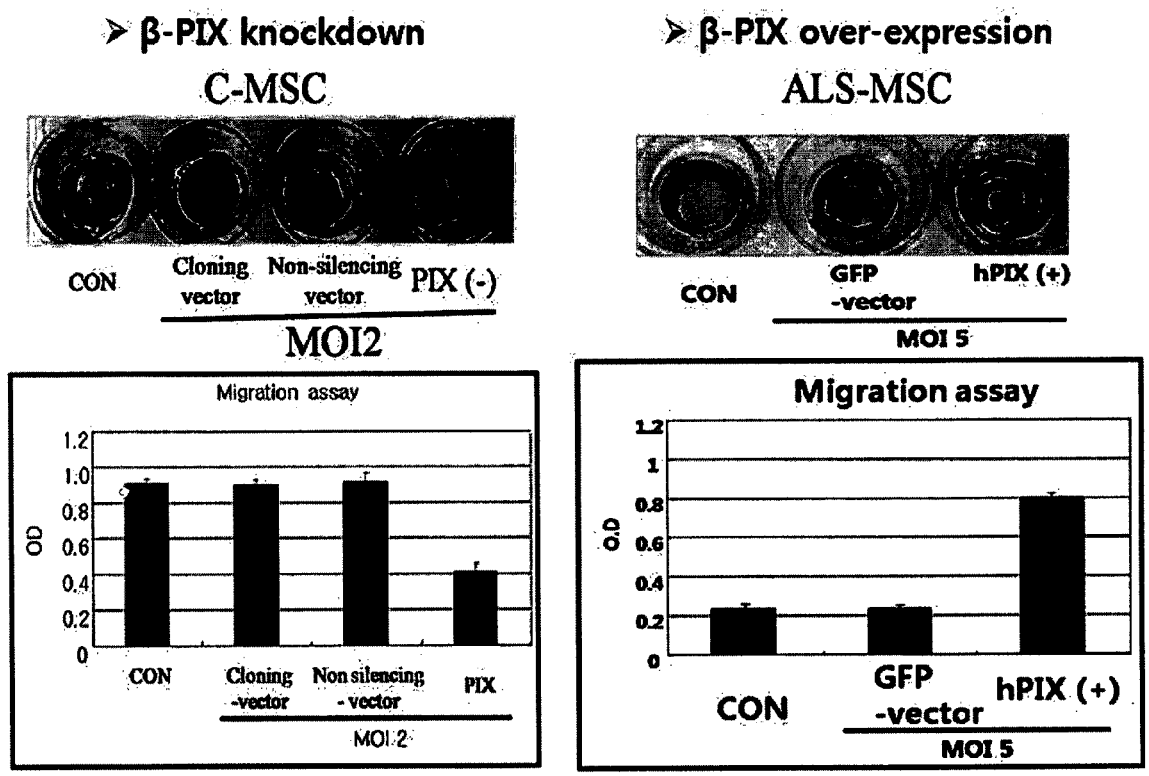

To determine whether β-PIX is required for MSC migration, we prepared C-MSCs with β-PIX knockdown by lentiviral-transduced shRNA, and ALS-MSCs ectopically expressing β-PIX The knockdown model had reduced levels of β-PIX mRNA and protein (FIG. 3a). β-PIX was over-expressed in ALS-MSCs transduced with lentiviral DNAs bearing the β-PIX cDNAs PIX (FIG. 3b). The changes in β-PIX expression levels did not affect the MSC surface marker CD45-CD34-CD29+CD73+CD105+CD44+HLA-DR-phenotype (FIG. 8). However, the ALS-MSCs with over-expressed β-PIX had restored migratory capacity, whereas the β-PIX knockdown C-MSCs had drastically reduced migratory capacity as determined by an in vitro transwell chemotaxis assay (FIG. 3c). These results establish β-PIX as a facilitator of MSC migration.

Figure 4A:
FIG. 4 shows that In vivo migratory capacity of MSCs depends upon expression levels of β-PIX. The migration of human MSCs to lesion sites in the rat stroke model was assessed with MR imaging. β-PIX depleted C-MSCs did not migrate to lesion sites, while mock treated C-MSC did (FIG. 4a). β-PIX over-expression restored the ability of ALS-MSCs to migrate to lesion sites (FIG. 4b).
Figure 4A:
Figure 4B:
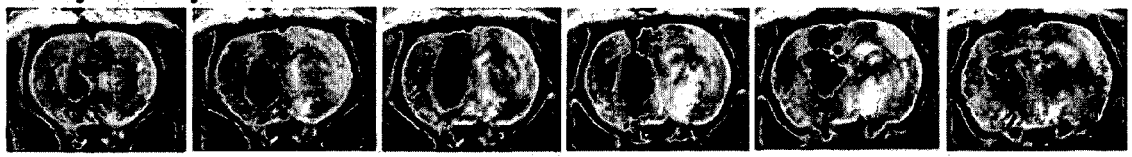
Figure 4B:
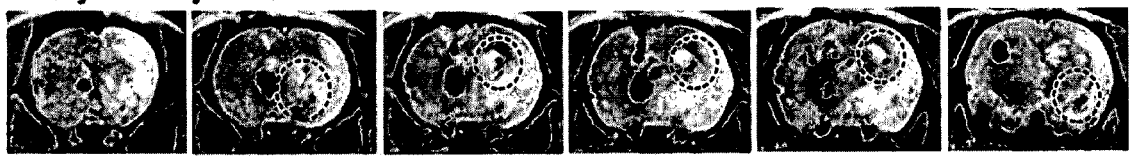

We next examined the in vivo migration of ALS-MSCs over-expressing β-PIX and CMSCs with β-PIX knockdown. These MSCs were implanted into rat brains subjected to ischemic stroke. T2*-weighted images of rat brains confirmed the in vitro finding that β-PIX expression is necessary for MSC migration (FIG. 4a-4b). The β-PIX knockdown CMSCs showed much lower levels of migration (2 out of 10) into the ischemic focus than CMSCs (8 of 10) (FIG. 4a). However, migration was enhanced by β-PIX over-expression in ALS-MSCs (7 of 10) and detected on MRI in comparison to ALS-MSCs (1 of 10) (FIG. 4b).

5. Western Blot and Immunocellularchemical Assay

Figure 2B:
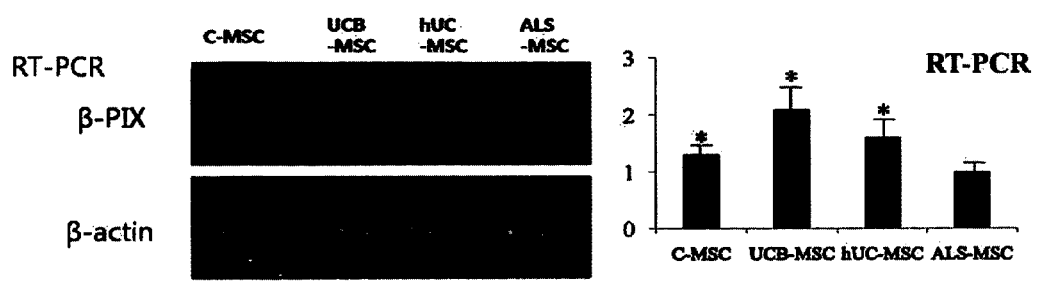
FIG. 2 represents expression levels of β-PIX and migration-associated factors in MSCs from different origins. β-PIX and some migration-associated gene expression levels were lower in ALS-MSC than C-MSC as assessed by quantitative PCR array (FIG. 2a). Expression levels of mRNA (FIG. 2b) and protein (FIGS. 2c and 2d) were lowest in ALS-MSC.
Figure 2C:
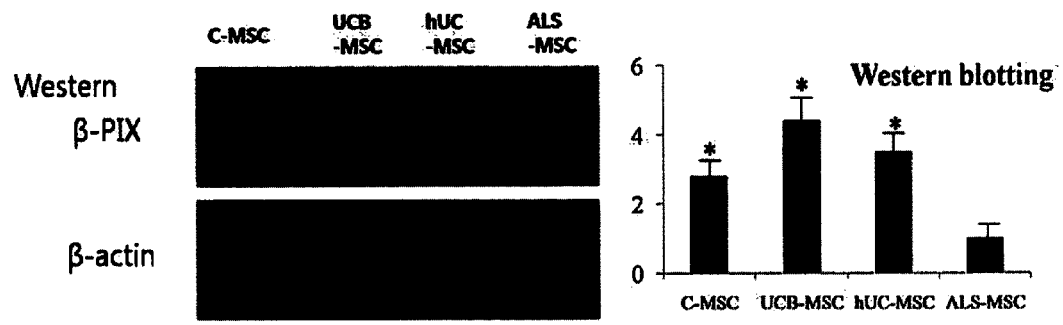
Figure 2D:
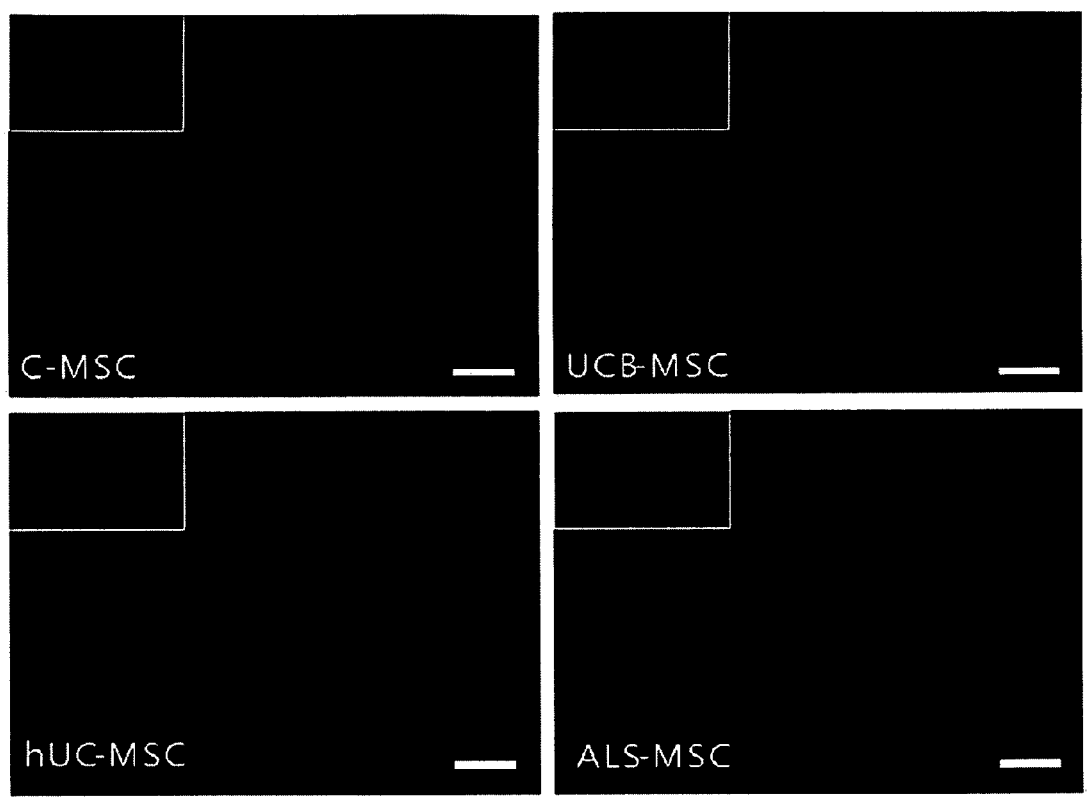

We next determined whether β-PIX mRNA and protein expression levels were correlated with the migratory activity of MSCs using RT-PCR, immunoblotting, and immunohistochemistry (FIG. 2). The expression levels of β-PIX mRNA and protein were significantly higher in C-MSCs, UCB-MSCs, and hUC-MSCs than ALS-MSCs (FIG. 2b-2d). Thus decreased expression of β-PIX mRNA and protein was associated with decreased migratory capacity of MSCs.

6. Comparison of Behavioral Functions between β-PIX Knockdowned and Vehicle C-MSCs.

Figure 9:
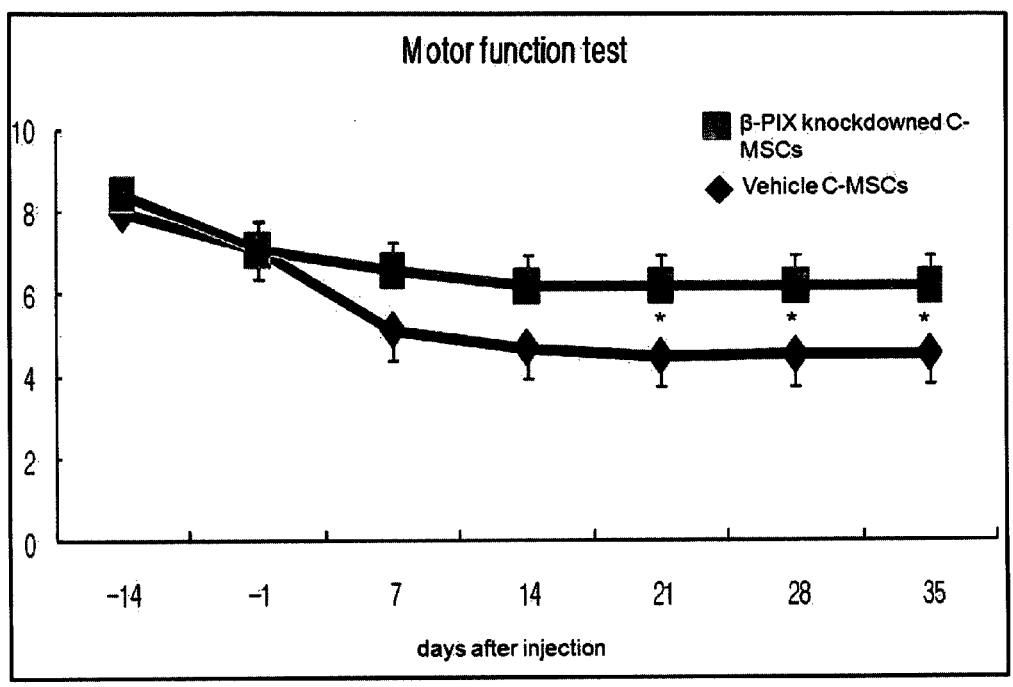
FIG. 9 represents the comparison of behavioral functions between β-PIX knockdowned and vehicle C-MSCs. The neurologic examination was performed daily as above described after the implantation of β-PIX knockdowned and vehicle C-MSCs. As shown in this figure, there was no improvement in behavioral functions of the ischemic stroke rats (N=10) implanted with β-PIX knockdowned C-MSCs when compared with the rats (N=10) implanted with vehicle C-MSCs. In other words, β-PIX knockdowned C-MSCs did not improve behavioral functions of ischemic stroke rats but vehicle C-MSCs did. [*p<0.05 when compared with the PBS group, Wilcoxon Scores (Rank Sums)].

We next determined if the migration of the implanted MSCs into the lesion site improved motor function recovery for the ischemic stroke rats. The rats that received β-PIX knockdown C-MSCs did not demonstrate any neurological function recovery, whereas rats that received C-MSCs transplant did show improvement (FIG. 9). Moreover, rats that received β-PIX over-expressing ALS-MSCs did not improve neurological functions and was similar to ALS-MSCs transplant rats. These results suggested that the migration of the implanted MSCs was necessary, but insufficient, for the ability of MSC transplants to improve motor functions of ischemic stroke rats.

7. Comparison of Neurotrophic Factors.

Figure 10A:
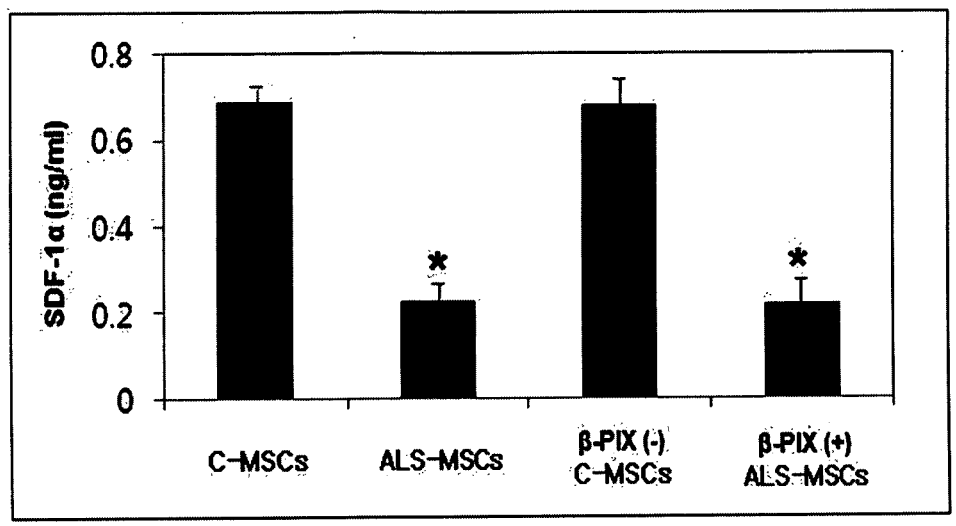
FIG. 10 represents comparison of neurotrophic factors. When compared with C-MSCs, concentrations of SDF-1α (A) and VEGF (B) were significantly decreased in culture supernatant of ALS-MSCs but concentration of BDNF (C) was not. The level of these neurotrophic factors is not affected by genetic modulation of β-PIX.
Figure 10B:
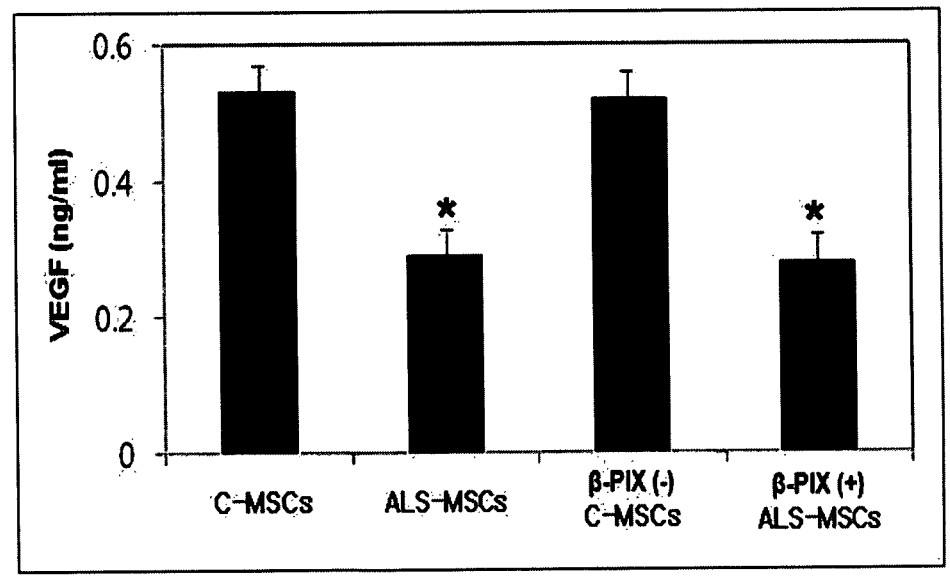
Figure 10C:
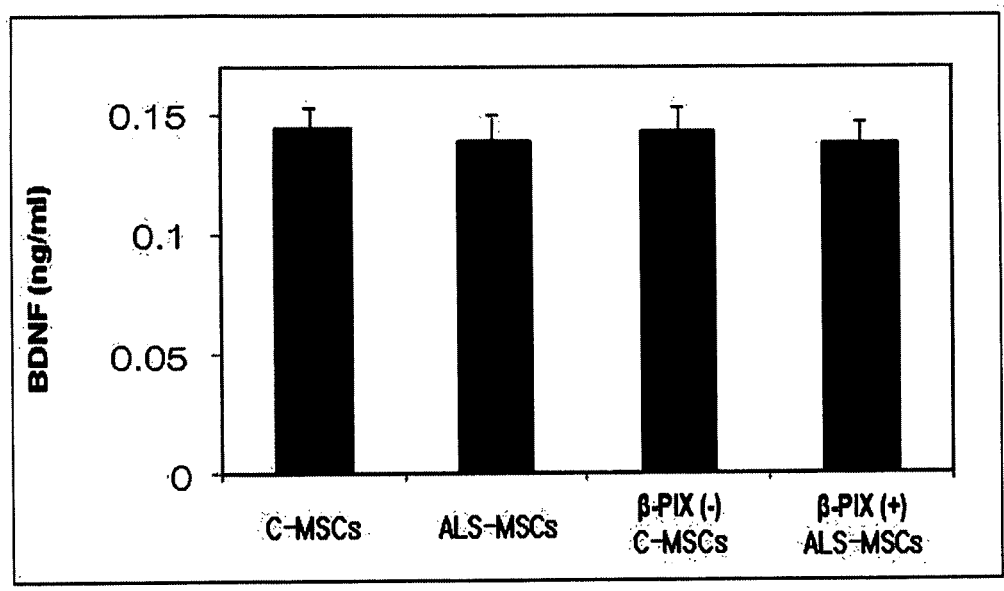
Figure 11:
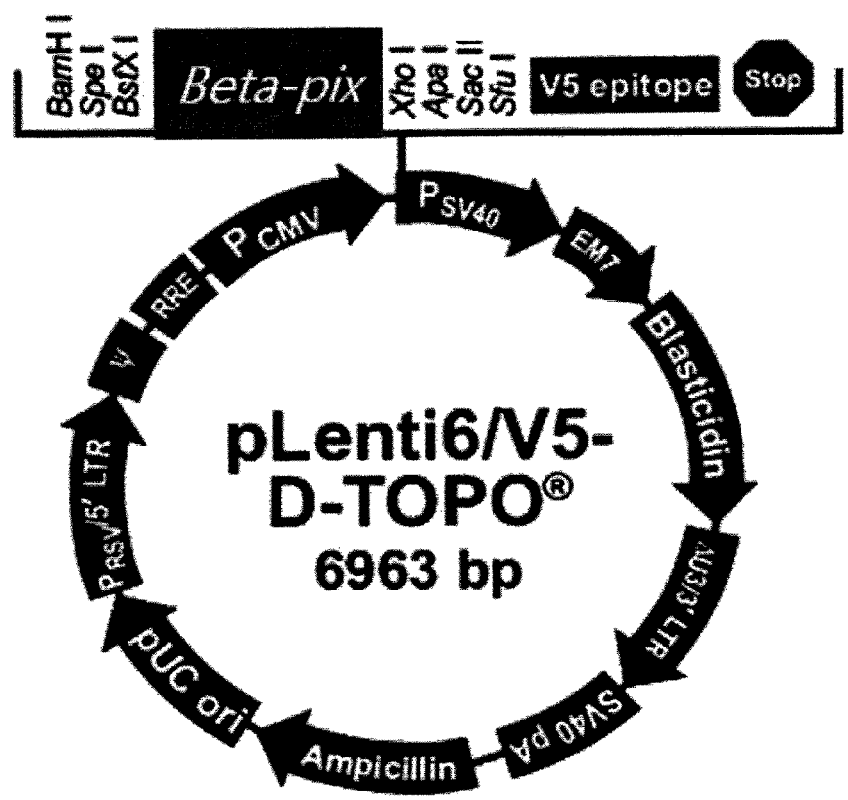
FIG. 11 shows the vector map of pLenti6/V5-D-TOPO used in cloning β-PIX.

We found that the levels of two neurotrophic factors, SDF-1α and VEGF, were significantly lower for ALS-MSCs than for C-MSCs (Supplementary FIG. 6A, 6B). However, β-PIX knockdown in C-MSCs or over-expression in ALS-MSCs did not affect SDF-1α or VEGF expression levels (FIG. 10a-10b). Thus, autologous ALS-MSC transplants would be expected to require both β-PIX over-expression and supplementation of neurotrophic factors such as SDF-1α and VEGF to restore stem cell migration toward lesion sites that is needed for the improvement of motor function.

References

1. Graziano, A. et al., Concave pit-containing scaffold surfaces improve stem cell derived osteoblast performance and lead to significant bone tissue formation. *PLoS ONE* 2 (6), e496 (2007).
2. Lambrechts, D. et al., VEGF is a modifier of amyotrophic lateral sclerosis in mice and humans and protects motoneurons against ischemic death. *Nat Genet* 34 (4), 383(2003).
3. Volinsky, N., Gantman, A., and Yablonski, D., A Pak- and Pix-dependent branch of the SDF-1alpha signalling pathway mediates T cell chemotaxis across restrictive barriers. *Biochem J* 397 (1), 213 (2006).
4. ten Klooster, J. P., Jaffer, Z. M., Chernoff, J., and Hordijk, P. L., Targeting and activation of Rac1 are mediated by the exchange factor beta-Pix. *J Cell Biol* 172 (5), 759 (2006).
5. Shin, E. Y. et al., Phosphorylation of p85 beta PIX, a Rac/Cdc42-specific guanine nucleotide exchange factor, via the Ras/ERK/PAK2 pathway is required for basic fibroblast growth factor-induced neurite outgrowth. *J Biol Chem* 277(46), 44417(2002).
6. Mazzini, L. et al., Stem cell treatment in Amyotrophic Lateral Sclerosis. *J Neurol Sci* 265 (1-2), 78 (2008).

7. Kim, H. Y. et al., Efficacy and Safety of Autologous Bone Marrow-derived Mesenchymal Stem Cell Treatment in Patients with Amyotrophic Lateral Sclerosis. *J Korean Neurol Assoc* 27 (2), 163 (2009).
8. Koh, S. H. et al., Implantation of human umbilical cord-derived mesenchymal stem cells as a neuroprotective therapy for ischemic stroke in rats. *Brain Res* 1229, 233 (2008).
9. Omura, T. et al., Effect of a new inhibitor of the synthesis of 20-HETE on cerebral ischemia reperfusion injury. *Stroke* 37 (5), 1307 (2006).
10. Ko, I. K. et al., In vivo MR imaging of tissue-engineered human mesenchymal stem cells transplanted to mouse: a preliminary study. *Ann Biomed Eng* 35 (1), 101 (2007).
11. Arbab, A. S. et al., Efficient magnetic cell labeling with protamine sulfate complexed to ferumoxides for cellular MRI. *Blood* 104 (4), 1217 (2004).
12. Koh, S. H. et al., Erythropoietin increases the motility of human bone marrow multipotent stromal cells (hBM-MSCs) and enhances the production of neurotrophic factors from hBM-MSCs. *Stem Cells Dev* (2009).

---

What is claimed is:

1. A method for improving the migration potential of a mesenchymal stem cell, comprising introducing into the mesenchymal stem cell a gene delivery system that expresses a nucleotide sequence encoding β-PIX having the amino acid sequence of SEQ ID NO:2 in the mesenchymal stem cell, wherein expression of said nucleotide sequence improves the migration potential of said mesenchymal stem cell when compared to a mesenchymal stem cell that does not express said nucleotide sequence.

2. The method according to claim 1, wherein the nucleotide sequence is SEQ ID NO: 1.

3. The method according to claim 1, wherein the gene delivery system is a plasmid, a recombinant adenovirus, an adeno-associated virus (AAV), a retrovirus, a lentivirus, a herpesvirus, a vaccinia virus, a liposome or a niosome.

4. The method according to claim 3, wherein the gene delivery system is the lentivirus.

* * * * *

SEQUENCE LISTING

```
<160> NUMBER OF SEQ ID NOS: 2

<210> SEQ ID NO 1
<211> LENGTH: 1941
<212> TYPE: DNA
<213> ORGANISM: Homo sapiens
<220> FEATURE:
<221> NAME/KEY: CDS
<222> LOCATION: (4)..(1938)

<400> SEQUENCE: 1 atg acc gat aat agc aac aat caa ctg gta gta aga gca aag ttt aac        48
    Thr Asp Asn Ser Asn Asn Gln Leu Val Val Arg Ala Lys Phe Asn
    1               5                   10                  15 ttc cag cag acc aat gag gac gag ctt tcc ttc tca aaa gga gac gtc        96
Phe Gln Gln Thr Asn Glu Asp Glu Leu Ser Phe Ser Lys Gly Asp Val
                20                  25                  30 atc cat gtc acc cgt gtg gaa gag gga ggc tgg tgg gag ggc aca ctc       144
Ile His Val Thr Arg Val Glu Glu Gly Gly Trp Trp Glu Gly Thr Leu
            35                  40                  45 aac ggc cgg acc ggc tgg ttc ccc agc aac tac gtg cgc gag gtc aag       192
Asn Gly Arg Thr Gly Trp Phe Pro Ser Asn Tyr Val Arg Glu Val Lys
        50                  55                  60 gcc agc gag aag cct gtg tct ccc aaa tca gga aca ctg aag agc cct       240
Ala Ser Glu Lys Pro Val Ser Pro Lys Ser Gly Thr Leu Lys Ser Pro
65                  70                  75 ccc aaa gga ttt gat acg act gcc ata aac aaa agc tat tac aat gtg       288
Pro Lys Gly Phe Asp Thr Thr Ala Ile Asn Lys Ser Tyr Tyr Asn Val
80                  85                  90                  95 gtg cta cag aat att tta gaa aca gaa aat gaa tat tct aaa gaa ctt       336
Val Leu Gln Asn Ile Leu Glu Thr Glu Asn Glu Tyr Ser Lys Glu Leu
                100                 105                 110 cag act gtg ctt tca acg tac cta cgg cca ttg cag acc agt gag aag       384
Gln Thr Val Leu Ser Thr Tyr Leu Arg Pro Leu Gln Thr Ser Glu Lys
            115                 120                 125 tta agt tca gca aac att tca tat tta atg gga aat cta gaa gaa ata       432
Leu Ser Ser Ala Asn Ile Ser Tyr Leu Met Gly Asn Leu Glu Glu Ile
        130                 135                 140 tgt tct ttc cag caa atg ctc gta cag tct tta gaa gaa tgc acc aag       480
Cys Ser Phe Gln Gln Met Leu Val Gln Ser Leu Glu Glu Cys Thr Lys
145                 150                 155 ttg ccc gaa gct cag cag aga gtc gga ggc tgc ttt tta aac ctg atg       528
Leu Pro Glu Ala Gln Gln Arg Val Gly Gly Cys Phe Leu Asn Leu Met
160                 165                 170                 175 cca cag atg aaa acc ctg tac ctc acg tat tgt gcc aat cac cct tct       576
Pro Gln Met Lys Thr Leu Tyr Leu Thr Tyr Cys Ala Asn His Pro Ser
                180                 185                 190 gca gtg aat gtc ctc acg gaa cac agt gag gag ttg ggg gag ttc atg       624
Ala Val Asn Val Leu Thr Glu His Ser Glu Glu Leu Gly Glu Phe Met
            195                 200                 205
```

-continued

| | | | | | | | | | | | | | | | | |
|---|---|---|---|---|---|---|---|---|---|---|---|---|---|---|---|---|
| gag | acc | aaa | ggt | gcc | agc | agc | cct | ggg | att | ctc | gtg | ctg | acc | acg | ggc | 672 |
| Glu | Thr | Lys | Gly | Ala | Ser | Ser | Pro | Gly | Ile | Leu | Val | Leu | Thr | Thr | Gly | |
| | 210 | | | | | 215 | | | | | 220 | | | | | |
| ctg | agc | aaa | ccc | ttc | atg | cgc | ctg | gat | aaa | tac | cct | acg | ctg | ctc | aaa | 720 |
| Leu | Ser | Lys | Pro | Phe | Met | Arg | Leu | Asp | Lys | Tyr | Pro | Thr | Leu | Leu | Lys | |
| 225 | | | | | 230 | | | | | 235 | | | | | | |
| gag | ctc | gag | aga | cac | atg | gag | gat | tat | cat | aca | gat | aga | caa | gat | att | 768 |
| Glu | Leu | Glu | Arg | His | Met | Glu | Asp | Tyr | His | Thr | Asp | Arg | Gln | Asp | Ile | |
| 240 | | | | | 245 | | | | | 250 | | | | | 255 | |
| caa | aaa | tcc | atg | gct | gcc | ttc | aaa | aac | ctt | tca | gcc | caa | tgt | caa | gaa | 816 |
| Gln | Lys | Ser | Met | Ala | Ala | Phe | Lys | Asn | Leu | Ser | Ala | Gln | Cys | Gln | Glu | |
| | | | 260 | | | | | 265 | | | | | 270 | | | |
| gtc | cgg | aag | agg | aaa | gag | ctt | gag | ctg | cag | atc | ctg | acg | gaa | gcc | atc | 864 |
| Val | Arg | Lys | Arg | Lys | Glu | Leu | Glu | Leu | Gln | Ile | Leu | Thr | Glu | Ala | Ile | |
| | | 275 | | | | | 280 | | | | | 285 | | | | |
| cgg | aac | tgg | gag | ggc | gat | gac | att | aaa | act | ctg | ggc | aac | gtc | act | tac | 912 |
| Arg | Asn | Trp | Glu | Gly | Asp | Asp | Ile | Lys | Thr | Leu | Gly | Asn | Val | Thr | Tyr | |
| | 290 | | | | | 295 | | | | | 300 | | | | | |
| atg | tcc | cag | gtc | ctg | att | cag | tgt | gcc | gga | agt | gag | gaa | aag | aat | gaa | 960 |
| Met | Ser | Gln | Val | Leu | Ile | Gln | Cys | Ala | Gly | Ser | Glu | Glu | Lys | Asn | Glu | |
| 305 | | | | | 310 | | | | | 315 | | | | | | |
| aga | tat | ctt | cta | ctc | ttc | cca | aat | gtt | ttg | cta | atg | ttg | tct | gcc | agt | 1008 |
| Arg | Tyr | Leu | Leu | Leu | Phe | Pro | Asn | Val | Leu | Leu | Met | Leu | Ser | Ala | Ser | |
| 320 | | | | | 325 | | | | | 330 | | | | | 335 | |
| cct | agg | atg | agt | ggc | ttt | atc | tat | cag | gga | aag | ctt | cca | acg | aca | gga | 1056 |
| Pro | Arg | Met | Ser | Gly | Phe | Ile | Tyr | Gln | Gly | Lys | Leu | Pro | Thr | Thr | Gly | |
| | | | 340 | | | | | 345 | | | | | 350 | | | |
| atg | aca | atc | aca | aag | ctt | gag | gac | agt | gaa | aat | cat | aga | aat | gca | ttt | 1104 |
| Met | Thr | Ile | Thr | Lys | Leu | Glu | Asp | Ser | Glu | Asn | His | Arg | Asn | Ala | Phe | |
| | | 355 | | | | | 360 | | | | | 365 | | | | |
| gaa | ata | tca | ggg | agc | atg | att | gag | cgg | ata | tta | gtg | tcg | tgc | aac | aac | 1152 |
| Glu | Ile | Ser | Gly | Ser | Met | Ile | Glu | Arg | Ile | Leu | Val | Ser | Cys | Asn | Asn | |
| | 370 | | | | | 375 | | | | | 380 | | | | | |
| cag | cag | gat | ctg | cag | gaa | tgg | gtg | gag | cac | cta | cag | aag | caa | acg | aag | 1200 |
| Gln | Gln | Asp | Leu | Gln | Glu | Trp | Val | Glu | His | Leu | Gln | Lys | Gln | Thr | Lys | |
| 385 | | | | | 390 | | | | | 395 | | | | | | |
| gtc | acg | tct | gtg | gga | aac | ccc | acc | ata | aag | cct | cat | tca | gtg | cca | tct | 1248 |
| Val | Thr | Ser | Val | Gly | Asn | Pro | Thr | Ile | Lys | Pro | His | Ser | Val | Pro | Ser | |
| 400 | | | | | 405 | | | | | 410 | | | | | 415 | |
| cat | acc | ctc | ccc | tcc | cac | ccg | gtc | act | ccg | tcc | agc | aag | cac | gca | gac | 1296 |
| His | Thr | Leu | Pro | Ser | His | Pro | Val | Thr | Pro | Ser | Ser | Lys | His | Ala | Asp | |
| | | | 420 | | | | | 425 | | | | | 430 | | | |
| agc | aag | ccc | gcg | ccg | ctg | acg | ccc | gcc | tac | cac | acg | ctg | ccc | cac | ccc | 1344 |
| Ser | Lys | Pro | Ala | Pro | Leu | Thr | Pro | Ala | Tyr | His | Thr | Leu | Pro | His | Pro | |
| | | 435 | | | | | 440 | | | | | 445 | | | | |
| tcc | cac | cac | ggc | acc | ccg | cac | acc | acc | atc | aac | tgg | gga | ccc | ctg | gag | 1392 |
| Ser | His | His | Gly | Thr | Pro | His | Thr | Thr | Ile | Asn | Trp | Gly | Pro | Leu | Glu | |
| | 450 | | | | | 455 | | | | | 460 | | | | | |
| cct | ccg | aaa | aca | ccc | aag | ccc | tgg | agc | ctg | agc | tgc | ctg | cgg | ccc | gcg | 1440 |
| Pro | Pro | Lys | Thr | Pro | Lys | Pro | Trp | Ser | Leu | Ser | Cys | Leu | Arg | Pro | Ala | |
| | | 465 | | | | | 470 | | | | | 475 | | | | |
| cct | ccc | ctc | cgg | ccc | tca | gct | gct | ctc | tgc | tac | aag | gag | gat | ctt | agt | 1488 |
| Pro | Pro | Leu | Arg | Pro | Ser | Ala | Ala | Leu | Cys | Tyr | Lys | Glu | Asp | Leu | Ser | |
| 480 | | | | | 485 | | | | | 490 | | | | | 495 | |
| aag | agc | cct | aag | acc | atg | aaa | aag | ctg | ctg | ccc | aag | cgc | aaa | cct | gaa | 1536 |
| Lys | Ser | Pro | Lys | Thr | Met | Lys | Lys | Leu | Leu | Pro | Lys | Arg | Lys | Pro | Glu | |
| | | | 500 | | | | | 505 | | | | | 510 | | | |
| cgg | aag | cct | tca | gat | gag | gag | ttc | gcg | tcc | cgg | aaa | agc | aca | gct | gct | 1584 |
| Arg | Lys | Pro | Ser | Asp | Glu | Glu | Phe | Ala | Ser | Arg | Lys | Ser | Thr | Ala | Ala | |
| | | 515 | | | | | 520 | | | | | 525 | | | | |

```
ttg gaa gaa gat gct cag att ctg aaa gtc att gaa gct tac tgc acc        1632
Leu Glu Glu Asp Ala Gln Ile Leu Lys Val Ile Glu Ala Tyr Cys Thr
            530                 535                 540 agc gcc aaa aca agg caa aca ctc aat tca agt tca cgc aaa gaa tct        1680
Ser Ala Lys Thr Arg Gln Thr Leu Asn Ser Ser Ser Arg Lys Glu Ser
545                 550                 555 gct cca caa gtt ttg ctt cca gaa gaa gag aaa att ata gtg gaa gaa        1728
Ala Pro Gln Val Leu Leu Pro Glu Glu Glu Lys Ile Ile Val Glu Glu
560                 565                 570                 575 act aaa agt aat ggt cag aca gtg ata gaa gaa aag agt ctt gtg gat        1776
Thr Lys Ser Asn Gly Gln Thr Val Ile Glu Glu Lys Ser Leu Val Asp
            580                 585                 590 acc gta tat gca tta aag gat gaa gtt caa gaa tta aga cag gac aac        1824
Thr Val Tyr Ala Leu Lys Asp Glu Val Gln Glu Leu Arg Gln Asp Asn
            595                 600                 605 aaa aag atg aag aaa tct cta gag gaa gaa cag aga gcc cgc aaa gac        1872
Lys Lys Met Lys Lys Ser Leu Glu Glu Glu Gln Arg Ala Arg Lys Asp
                610                 615                 620 ctg gag aag ctg gtg agg aaa gtc ctg aag aac atg aat gat cct gcc        1920
Leu Glu Lys Leu Val Arg Lys Val Leu Lys Asn Met Asn Asp Pro Ala
625                 630                 635 tgg gat gag acc aat cta taa                                            1941
Trp Asp Glu Thr Asn Leu
640             645

<210> SEQ ID NO 2
<211> LENGTH: 645
<212> TYPE: PRT
<213> ORGANISM: Homo sapiens

<400> SEQUENCE: 2

Thr Asp Asn Ser Asn Asn Gln Leu Val Val Arg Ala Lys Phe Asn Phe
1               5                   10                  15

Gln Gln Thr Asn Glu Asp Glu Leu Ser Phe Ser Lys Gly Asp Val Ile
                20                  25                  30

His Val Thr Arg Val Glu Glu Gly Gly Trp Trp Glu Gly Thr Leu Asn
            35                  40                  45

Gly Arg Thr Gly Trp Phe Pro Ser Asn Tyr Val Arg Glu Val Lys Ala
        50                  55                  60

Ser Glu Lys Pro Val Ser Pro Lys Ser Gly Thr Leu Lys Ser Pro Pro
65                  70                  75                  80

Lys Gly Phe Asp Thr Thr Ala Ile Asn Lys Ser Tyr Tyr Asn Val Val
                85                  90                  95

Leu Gln Asn Ile Leu Glu Thr Glu Asn Glu Tyr Ser Lys Glu Leu Gln
                100                 105                 110

Thr Val Leu Ser Thr Tyr Leu Arg Pro Leu Gln Thr Ser Glu Lys Leu
            115                 120                 125

Ser Ser Ala Asn Ile Ser Tyr Leu Met Gly Asn Leu Glu Glu Ile Cys
        130                 135                 140

Ser Phe Gln Gln Met Leu Val Gln Ser Leu Glu Glu Cys Thr Lys Leu
145                 150                 155                 160

Pro Glu Ala Gln Gln Arg Val Gly Gly Cys Phe Leu Asn Leu Met Pro
                165                 170                 175

Gln Met Lys Thr Leu Tyr Leu Thr Tyr Cys Ala Asn His Pro Ser Ala
            180                 185                 190

Val Asn Val Leu Thr Glu His Ser Glu Glu Leu Gly Glu Phe Met Glu
            195                 200                 205
```

```
Thr Lys Gly Ala Ser Ser Pro Gly Ile Leu Val Leu Thr Thr Gly Leu
    210                 215                 220

Ser Lys Pro Phe Met Arg Leu Asp Lys Tyr Pro Thr Leu Leu Lys Glu
225                 230                 235                 240

Leu Glu Arg His Met Glu Asp Tyr His Thr Asp Arg Gln Asp Ile Gln
                245                 250                 255

Lys Ser Met Ala Ala Phe Lys Asn Leu Ser Ala Gln Cys Gln Glu Val
                260                 265                 270

Arg Lys Arg Lys Glu Leu Glu Leu Gln Ile Leu Thr Glu Ala Ile Arg
            275                 280                 285

Asn Trp Glu Gly Asp Asp Ile Lys Thr Leu Gly Asn Val Thr Tyr Met
    290                 295                 300

Ser Gln Val Leu Ile Gln Cys Ala Gly Ser Glu Glu Lys Asn Glu Arg
305                 310                 315                 320

Tyr Leu Leu Leu Phe Pro Asn Val Leu Leu Met Leu Ser Ala Ser Pro
                325                 330                 335

Arg Met Ser Gly Phe Ile Tyr Gln Gly Lys Leu Pro Thr Thr Gly Met
                340                 345                 350

Thr Ile Thr Lys Leu Glu Asp Ser Glu Asn His Arg Asn Ala Phe Glu
            355                 360                 365

Ile Ser Gly Ser Met Ile Glu Arg Ile Leu Val Ser Cys Asn Asn Gln
    370                 375                 380

Gln Asp Leu Gln Glu Trp Val Glu His Leu Gln Lys Gln Thr Lys Val
385                 390                 395                 400

Thr Ser Val Gly Asn Pro Thr Ile Lys Pro His Ser Val Pro Ser His
                405                 410                 415

Thr Leu Pro Ser His Pro Val Thr Pro Ser Ser Lys His Ala Asp Ser
                420                 425                 430

Lys Pro Ala Pro Leu Thr Pro Ala Tyr His Thr Leu Pro His Pro Ser
            435                 440                 445

His His Gly Thr Pro His Thr Thr Ile Asn Trp Gly Pro Leu Glu Pro
    450                 455                 460

Pro Lys Thr Pro Lys Pro Trp Ser Leu Ser Cys Leu Arg Pro Ala Pro
465                 470                 475                 480

Pro Leu Arg Pro Ser Ala Ala Leu Cys Tyr Lys Glu Asp Leu Ser Lys
                485                 490                 495

Ser Pro Lys Thr Met Lys Lys Leu Leu Pro Lys Arg Lys Pro Glu Arg
                500                 505                 510

Lys Pro Ser Asp Glu Glu Phe Ala Ser Arg Lys Ser Thr Ala Ala Leu
            515                 520                 525

Glu Glu Asp Ala Gln Ile Leu Lys Val Ile Glu Ala Tyr Cys Thr Ser
    530                 535                 540

Ala Lys Thr Arg Gln Thr Leu Asn Ser Ser Arg Lys Glu Ser Ala
545                 550                 555                 560

Pro Gln Val Leu Leu Pro Glu Glu Glu Lys Ile Ile Val Glu Glu Thr
                565                 570                 575

Lys Ser Asn Gly Gln Thr Val Ile Glu Glu Lys Ser Leu Val Asp Thr
                580                 585                 590

Val Tyr Ala Leu Lys Asp Glu Val Gln Glu Leu Arg Gln Asp Asn Lys
            595                 600                 605

Lys Met Lys Lys Ser Leu Glu Glu Glu Gln Arg Ala Arg Lys Asp Leu
    610                 615                 620
```

```
Glu Lys Leu Val Arg Lys Val Leu Lys Asn Met Asn Asp Pro Ala Trp
625                 630             635                 640

Asp Glu Thr Asn Leu
                645
```